(12) United States Patent    (10) Patent No.:   US 12,661,446 B2

Michaud et al.    (45) Date of Patent:   Jun. 23, 2026

---

(54) PATCH PUMP CARTRIDGE ATTACHMENT

(71) Applicant: Tandem Diabetes Care, Inc., San Diego, CA (US)

(72) Inventors: Michael Michaud, San Diego, CA (US); Philip Lamb, San Diego, CA (US); Michael Fitzgibbons, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 343 days.

(21) Appl. No.: 17/120,726

(22) Filed: Dec. 14, 2020

(65) Prior Publication Data

US 2021/0162117 A1   Jun. 3, 2021

Related U.S. Application Data

(63) Continuation of application No. 15/987,432, filed on May 23, 2018, now Pat. No. 10,864,318, which is a continuation of application No. 15/158,125, filed on May 18, 2016, now Pat. No. 9,993,595.

(60) Provisional application No. 62/163,158, filed on May 18, 2015.

(51) Int. Cl.
   *A61M 5/142*    (2006.01)
   *A61M 5/145*    (2006.01)
   *A61M 5/158*    (2006.01)

(52) U.S. Cl.
   CPC .... *A61M 5/14244* (2013.01); *A61M 5/14566* (2013.01); *A61M 5/14248* (2013.01); *A61M 2005/14252* (2013.01); *A61M 2005/14268*
(2013.01); *A61M 2005/14573* (2013.01); *A61M 2005/1585* (2013.01); *A61M 2205/12* (2013.01)

(58) Field of Classification Search
CPC .......... A61M 5/14248; A61M 5/14244; A61M 2005/14268; A61M 2205/3569
See application file for complete search history.

(56) References Cited

U.S. PATENT DOCUMENTS

| | | | |
|---|---|---|---|
| 4,559,038 A | 12/1985 | Berg et al. |
| 4,565,542 A | 1/1986 | Berg |
| 4,650,469 A | 3/1987 | Berg et al. |
| | (Continued) | | |

FOREIGN PATENT DOCUMENTS

| | | |
|---|---|---|
| CA | 2930776 C | 5/2018 |
| CN | 101745163 B | 12/2013 |
| | (Continued) | |

OTHER PUBLICATIONS

Application and File History for U.S. Appl. No. 15/158,125, filed May 18, 2016, inventors Michaud et al.

(Continued)

*Primary Examiner* — Laura A Bouchelle

(74) *Attorney, Agent, or Firm* — Merchant & Gould P.C.

(57) ABSTRACT

A user-wearable patch pump system for delivery of insulin or other medicament can include a patch pump having a reusable drive unit and a replaceable and refillable cartridge. The cartridge can selectively attach to and be detached from the drive unit. The cartridge can initially be inserted onto the drive unit in a first orientation at an angle to the drive unit and then be rotated to align the cartridge with the drive unit and lock the cartridge in place on the drive unit to form the patch pump.

17 Claims, 22 Drawing Sheets

(56)          References Cited

U.S. PATENT DOCUMENTS

| 4,878,896 | A | | 11/1989 | Garrison et al. |
| 4,893,966 | A | | 1/1990 | Roehl |
| 4,908,017 | A | | 3/1990 | Howson et al. |
| 5,090,963 | A | | 2/1992 | Gross et al. |
| 5,482,446 | A | | 1/1996 | Williamson et al. |
| 5,545,143 | A | * | 8/1996 | Fischell ............... A61M 5/158 |
| | | | | 604/180 |
| 5,551,850 | A | | 9/1996 | Williamson et al. |
| 5,676,651 | A | | 10/1997 | Larson, Jr. et al. |
| 5,935,099 | A | | 8/1999 | Peterson et al. |
| 6,013,020 | A | | 1/2000 | Meloul et al. |
| 6,143,252 | A | | 11/2000 | Haxo, Jr. et al. |
| 6,210,135 | B1 | | 4/2001 | Rassin et al. |
| 6,241,704 | B1 | | 6/2001 | Peterson et al. |
| 6,371,732 | B1 | | 4/2002 | Moubayed et al. |
| 6,423,035 | B1 | | 7/2002 | Das et al. |
| 6,475,180 | B2 | | 11/2002 | Peterson et al. |
| 6,482,186 | B1 | | 11/2002 | Douglas et al. |
| 6,485,461 | B1 | | 11/2002 | Mason et al. |
| 6,544,229 | B1 | | 4/2003 | Danby et al. |
| 6,610,003 | B1 | | 8/2003 | Meloul et al. |
| 6,641,566 | B2 | | 11/2003 | Douglas et al. |
| 6,656,148 | B2 | | 12/2003 | Das et al. |
| 6,683,690 | B1 | | 1/2004 | Tobias |
| 6,702,779 | B2 | | 3/2004 | Connelly et al. |
| 6,736,796 | B2 | | 5/2004 | Shekalim |
| 6,740,059 | B2 | * | 5/2004 | Flaherty ............ A61M 5/14248 |
| | | | | 607/151 |
| 6,744,350 | B2 | | 6/2004 | Blomquist |
| 6,852,104 | B2 | | 2/2005 | Blomquist |
| 6,918,542 | B2 | | 7/2005 | Silverbrook et al. |
| 6,923,764 | B2 | | 8/2005 | Aceti et al. |
| 6,940,209 | B2 | | 9/2005 | Henderson |
| 6,993,795 | B2 | | 2/2006 | Prineppi |
| 7,018,361 | B2 | | 3/2006 | Gillespie, Jr. et al. |
| 7,025,716 | B1 | | 4/2006 | Meloul et al. |
| 7,029,455 | B2 | | 4/2006 | Flaherty |
| 7,033,338 | B2 | | 4/2006 | Vilks et al. |
| 7,041,082 | B2 | | 5/2006 | Blomquist et al. |
| 7,073,713 | B2 | | 7/2006 | Silverbrook et al. |
| 7,083,108 | B2 | | 8/2006 | Silverbrook et al. |
| 7,092,011 | B2 | | 8/2006 | Silverbrook et al. |
| 7,097,104 | B2 | | 8/2006 | Silverbrook et al. |
| 7,107,706 | B1 | | 9/2006 | Bailey, Sr. et al. |
| 7,137,964 | B2 | | 11/2006 | Flaherty |
| 7,159,271 | B2 | | 1/2007 | Sepke et al. |
| 7,170,214 | B2 | | 1/2007 | Henderson et al. |
| 7,187,404 | B2 | | 3/2007 | Silverbrook et al. |
| 7,193,521 | B2 | | 3/2007 | Moberg et al. |
| 7,201,319 | B2 | | 4/2007 | Silverbrook et al. |
| 7,234,645 | B2 | | 6/2007 | Silverbrook et al. |
| 7,250,037 | B2 | | 7/2007 | Shermer et al. |
| 7,289,142 | B2 | | 10/2007 | Silverbrook |
| 7,306,555 | B2 | | 12/2007 | Dolecek et al. |
| 7,309,943 | B2 | | 12/2007 | Henderson et al. |
| 7,339,306 | B2 | | 3/2008 | Henderson |
| 7,347,836 | B2 | | 3/2008 | Peterson et al. |
| 7,362,971 | B2 | | 4/2008 | Silverbrook et al. |
| 7,373,083 | B2 | | 5/2008 | Silverbrook et al. |
| 7,373,690 | B2 | | 5/2008 | Sepke et al. |
| 7,377,706 | B2 | | 5/2008 | Silverbrook et al. |
| 7,390,314 | B2 | | 6/2008 | Stutz, Jr. et al. |
| 7,442,186 | B2 | | 10/2008 | Blomquist |
| 7,455,663 | B2 | | 11/2008 | Bikovsky |
| 7,460,152 | B2 | | 12/2008 | Silverbrook et al. |
| 7,475,825 | B2 | | 1/2009 | Silverbrook et al. |
| 7,483,050 | B2 | | 1/2009 | Silverbrook et al. |
| 7,497,827 | B2 | | 3/2009 | Brister et al. |
| 7,510,544 | B2 | | 3/2009 | Vilks et al. |
| 7,515,060 | B2 | | 4/2009 | Blomquist |
| 7,524,045 | B2 | | 4/2009 | Silverbrook et al. |
| 7,534,226 | B2 | | 5/2009 | Mernoe et al. |
| 7,569,050 | B2 | | 8/2009 | Moberg et al. |
| 7,608,060 | B2 | | 10/2009 | Gillespie, Jr. et al. |
| 7,621,893 | B2 | | 11/2009 | Moberg et al. |
| 7,641,649 | B2 | | 1/2010 | Moberg et al. |
| 7,654,976 | B2 | | 2/2010 | Peterson et al. |
| 7,682,338 | B2 | | 3/2010 | Griffin |
| 7,686,787 | B2 | | 3/2010 | Moberg et al. |
| 7,699,833 | B2 | | 4/2010 | Moberg et al. |
| 7,708,717 | B2 | | 5/2010 | Estes et al. |
| 7,711,402 | B2 | | 5/2010 | Shults et al. |
| 7,713,238 | B2 | | 5/2010 | Mernoe |
| 7,736,338 | B2 | | 6/2010 | Kavazov et al. |
| 7,736,344 | B2 | | 6/2010 | Moberg et al. |
| 7,737,581 | B2 | | 6/2010 | Spurlin et al. |
| 7,744,589 | B2 | | 6/2010 | Mounce et al. |
| 7,766,863 | B2 | | 8/2010 | Gillespie, Jr. et al. |
| 7,766,873 | B2 | | 8/2010 | Moberg et al. |
| 7,776,030 | B2 | | 8/2010 | Estes et al. |
| 7,785,288 | B2 | | 8/2010 | Mernøe et al. |
| 7,786,648 | B2 | | 8/2010 | Xu et al. |
| 7,789,857 | B2 | | 9/2010 | Moberg et al. |
| 7,794,426 | B2 | | 9/2010 | Briones et al. |
| 7,794,427 | B2 | | 9/2010 | Estes et al. |
| 7,794,428 | B2 | | 9/2010 | Estes et al. |
| 7,806,868 | B2 | | 10/2010 | De Polo et al. |
| 7,828,771 | B2 | | 11/2010 | Chiang et al. |
| 7,833,196 | B2 | | 11/2010 | Estes et al. |
| 7,887,511 | B2 | | 2/2011 | Mernøe et al. |
| 7,887,512 | B2 | | 2/2011 | Estes et al. |
| 7,892,199 | B2 | | 2/2011 | Mhatre et al. |
| 7,892,206 | B2 | | 2/2011 | Moberg et al. |
| 7,905,859 | B2 | | 3/2011 | Bynum et al. |
| 7,905,868 | B2 | | 3/2011 | Moberg et al. |
| 7,938,803 | B2 | | 5/2011 | Mernoe et al. |
| 7,955,305 | B2 | | 6/2011 | Moberg et al. |
| 7,963,954 | B2 | | 6/2011 | Kavazov |
| 7,981,084 | B2 | | 7/2011 | Estes et al. |
| 7,981,102 | B2 | | 7/2011 | Patel et al. |
| 7,998,111 | B2 | | 8/2011 | Moberg et al. |
| 8,007,460 | B2 | | 8/2011 | Gelfand et al. |
| 8,062,257 | B2 | | 11/2011 | Moberg et al. |
| 8,065,096 | B2 | | 11/2011 | Moberg et al. |
| 8,105,279 | B2 | | 1/2012 | Mernoe et al. |
| 8,106,534 | B2 | | 1/2012 | Spurlin et al. |
| 8,109,912 | B2 | | 2/2012 | Alferness et al. |
| 8,147,451 | B2 | | 4/2012 | Brockman et al. |
| 8,149,131 | B2 | | 4/2012 | Blomquist |
| 8,156,070 | B2 | | 4/2012 | Buck et al. |
| 8,157,769 | B2 | | 4/2012 | Cabiri |
| 8,177,739 | B2 | | 5/2012 | Cartledge et al. |
| 8,182,447 | B2 | | 5/2012 | Moberg et al. |
| 8,211,062 | B2 | | 7/2012 | Estes et al. |
| 8,217,533 | B2 | | 7/2012 | Jones et al. |
| 8,231,562 | B2 | | 7/2012 | Buck et al. |
| 8,237,715 | B2 | | 8/2012 | Buck et al. |
| 8,250,483 | B2 | | 8/2012 | Blomquist |
| 8,267,893 | B2 | | 9/2012 | Moberg et al. |
| 8,267,921 | B2 | | 9/2012 | Yodfat et al. |
| 8,277,415 | B2 | | 10/2012 | Mounce et al. |
| 8,282,601 | B2 | | 10/2012 | Mernoe et al. |
| 8,287,495 | B2 | | 10/2012 | Michaud et al. |
| 8,287,514 | B2 | | 10/2012 | Miller et al. |
| 8,298,184 | B2 | | 10/2012 | Diperna et al. |
| 8,299,733 | B2 | | 10/2012 | Sattler et al. |
| 8,304,960 | B2 | | 11/2012 | Sattler et al. |
| 8,310,415 | B2 | | 11/2012 | McLaughlin et al. |
| 8,311,749 | B2 | | 11/2012 | Brauker et al. |
| 8,317,752 | B2 | | 11/2012 | Cozmi et al. |
| 8,346,399 | B2 | | 1/2013 | Blomquist |
| 8,414,563 | B2 | | 4/2013 | Kamen et al. |
| 8,435,206 | B2 | | 5/2013 | Evans et al. |
| 8,444,595 | B2 | | 5/2013 | Brukalo et al. |
| 8,449,523 | B2 | | 5/2013 | Brukalo et al. |
| 8,450,905 | B2 | | 5/2013 | Guidarelli et al. |
| 8,452,953 | B2 | | 5/2013 | Buck et al. |
| 8,454,575 | B2 | | 6/2013 | Estes et al. |
| 8,466,637 | B2 | | 6/2013 | Guidarelli et al. |
| 8,469,920 | B2 | | 6/2013 | Mernoe et al. |
| 8,502,662 | B2 | | 8/2013 | Pohlman et al. |
| 8,552,880 | B2 | | 10/2013 | Kopp et al. |
| 8,568,361 | B2 | * | 10/2013 | Yodfat ................ A61M 5/1456 |
| | | | | 604/152 |

(56)                 References Cited

U.S. PATENT DOCUMENTS

| | | | |
|---|---|---|---|
| 8,573,027 B2 | 11/2013 | Rosinko et al. | |
| 8,663,201 B2 | 3/2014 | Hill | |
| 8,740,847 B2 | 6/2014 | Levesque | |
| 8,758,323 B2 | 6/2014 | Michaud et al. | |
| 8,801,655 B2 | 8/2014 | Mernoe et al. | |
| 8,926,561 B2 | 1/2015 | Verhoef | |
| 8,932,250 B2 | 1/2015 | Montgomery | |
| 8,952,794 B2 | 2/2015 | Blomquist | |
| 8,986,253 B2 | 3/2015 | DiPerna | |
| 9,049,982 B2 | 6/2015 | Brukalo | |
| 9,132,227 B2 | 9/2015 | Bryant, Jr. | |
| 9,259,531 B2 | 2/2016 | Kamen et al. | |
| 9,308,319 B2 | 4/2016 | Mernoe et al. | |
| 9,362,851 B2 | 6/2016 | Xu et al. | |
| 9,474,856 B2 | 10/2016 | Blomquist | |
| 9,486,571 B2 | 11/2016 | Rosinko | |
| 9,565,718 B2 | 2/2017 | Swanson | |
| 9,737,656 B2 | 8/2017 | Rosinko | |
| 9,993,595 B2 | 6/2018 | Michaud et al. | |
| 10,213,547 B2 | 2/2019 | Rosinko | |
| 10,279,106 B1 | 5/2019 | Cook et al. | |
| 10,279,107 B2 | 5/2019 | Michaud | |
| 10,357,603 B2 | 7/2019 | Michaud et al. | |
| 10,430,043 B2 | 10/2019 | Rosinko et al. | |
| 10,478,551 B2 | 11/2019 | Rosinko | |
| 10,773,015 B2 | 9/2020 | Blomquist et al. | |
| 10,806,851 B2 | 10/2020 | Rosinko | |
| 10,864,318 B2 | 12/2020 | Michaud et al. | |
| 10,918,785 B2 | 2/2021 | Rosinko | |
| 10,926,025 B2 | 2/2021 | Betts et al. | |
| 2002/0072733 A1 | 6/2002 | Flaherty | |
| 2003/0088238 A1* | 5/2003 | Poulsen | A61M 5/1413 |
| | | | 604/890.1 |
| 2003/0160683 A1 | 8/2003 | Blomquist | |
| 2003/0163088 A1 | 8/2003 | Blomquist | |
| 2003/0163223 A1 | 8/2003 | Blomquist | |
| 2003/0163789 A1 | 8/2003 | Blomquist | |
| 2003/0212379 A1* | 11/2003 | Bylund | G16H 20/17 |
| | | | 700/282 |
| 2005/0143864 A1 | 6/2005 | Blomquist | |
| 2005/0171512 A1 | 8/2005 | Flaherty | |
| 2006/0253086 A1 | 11/2006 | Moberg et al. | |
| 2006/0264835 A1 | 11/2006 | Nielsen et al. | |
| 2006/0272652 A1 | 12/2006 | Stocker et al. | |
| 2007/0049870 A1 | 3/2007 | Gray et al. | |
| 2007/0060869 A1 | 3/2007 | Tolle et al. | |
| 2007/0060870 A1 | 3/2007 | Tolle et al. | |
| 2007/0073236 A1 | 3/2007 | Mernoe et al. | |
| 2007/0093786 A1* | 4/2007 | Goldsmith | A61B 5/14532 |
| | | | 604/890.1 |
| 2007/0149926 A1 | 6/2007 | Moberg et al. | |
| 2007/0156092 A1 | 7/2007 | Estes et al. | |
| 2007/0161955 A1 | 7/2007 | Bynum et al. | |
| 2007/0167905 A1 | 7/2007 | Estes et al. | |
| 2007/0167912 A1 | 7/2007 | Causey et al. | |
| 2007/0173762 A1 | 7/2007 | Estes et al. | |
| 2007/0179444 A1 | 8/2007 | Causey et al. | |
| 2007/0219480 A1 | 9/2007 | Kamen et al. | |
| 2007/0219496 A1 | 9/2007 | Kamen et al. | |
| 2007/0219597 A1 | 9/2007 | Kamen et al. | |
| 2007/0228071 A1 | 10/2007 | Kamen et al. | |
| 2007/0233051 A1* | 10/2007 | Hohl | A61B 5/1486 |
| | | | 604/500 |
| 2008/0033360 A1 | 2/2008 | Evans et al. | |
| 2008/0033361 A1 | 2/2008 | Evans et al. | |
| 2008/0033402 A1 | 2/2008 | Blomquist | |
| 2008/0033749 A1 | 2/2008 | Blomquist | |
| 2008/0034323 A1 | 2/2008 | Blomquist | |
| 2008/0045902 A1 | 2/2008 | Estes et al. | |
| 2008/0045903 A1 | 2/2008 | Estes et al. | |
| 2008/0045904 A1 | 2/2008 | Estes et al. | |
| 2008/0045931 A1 | 2/2008 | Estes et al. | |
| 2008/0051711 A1 | 2/2008 | Mounce et al. | |
| 2008/0065007 A1 | 3/2008 | Peterson et al. | |
| 2008/0065016 A1 | 3/2008 | Peterson et al. | |
| 2008/0106431 A1 | 5/2008 | Blomquist | |
| 2008/0126969 A1 | 5/2008 | Blomquist | |
| 2008/0139910 A1 | 6/2008 | Mastrototaro et al. | |
| 2008/0171967 A1 | 7/2008 | Blomquist et al. | |
| 2008/0172026 A1 | 7/2008 | Blomquist | |
| 2008/0172027 A1 | 7/2008 | Blomquist | |
| 2008/0172028 A1 | 7/2008 | Blomquist | |
| 2008/0172029 A1 | 7/2008 | Blomquist | |
| 2008/0172030 A1 | 7/2008 | Blomquist | |
| 2008/0172031 A1 | 7/2008 | Blomquist | |
| 2008/0200900 A1 | 8/2008 | Aeschlimann et al. | |
| 2008/0215035 A1 | 9/2008 | Yodfat et al. | |
| 2008/0221523 A1 | 9/2008 | Moberg et al. | |
| 2008/0234663 A1* | 9/2008 | Yodfat | A61M 5/1723 |
| | | | 604/890.1 |
| 2008/0294094 A1 | 11/2008 | Mhatre et al. | |
| 2008/0294108 A1 | 11/2008 | Briones et al. | |
| 2008/0294109 A1 | 11/2008 | Estes et al. | |
| 2008/0294142 A1 | 11/2008 | Patel et al. | |
| 2008/0312584 A1 | 12/2008 | Montgomery | |
| 2009/0036870 A1 | 2/2009 | Mounce et al. | |
| 2009/0069749 A1 | 3/2009 | Miller et al. | |
| 2009/0082728 A1 | 3/2009 | Bikovsky | |
| 2009/0118592 A1 | 5/2009 | Klitgaard | |
| 2009/0171269 A1 | 7/2009 | Jennewine et al. | |
| 2009/0227855 A1 | 9/2009 | Hill et al. | |
| 2009/0254037 A1 | 10/2009 | Bryant, Jr. et al. | |
| 2009/0259183 A1 | 10/2009 | Chong et al. | |
| 2009/0259209 A1 | 10/2009 | Chong et al. | |
| 2009/0264825 A1 | 10/2009 | Cote et al. | |
| 2009/0270810 A1 | 10/2009 | Debelser et al. | |
| 2009/0270811 A1 | 10/2009 | Mounce et al. | |
| 2009/0270833 A1 | 10/2009 | Debelser et al. | |
| 2010/0016791 A1 | 1/2010 | Chong et al. | |
| 2010/0037680 A1 | 2/2010 | Moberg et al. | |
| 2010/0064257 A1 | 3/2010 | Buck et al. | |
| 2010/0100037 A1 | 4/2010 | Cozmi et al. | |
| 2010/0100048 A1 | 4/2010 | Nielsen et al. | |
| 2010/0145303 A1 | 6/2010 | Yodfat et al. | |
| 2010/0152674 A1 | 6/2010 | Kavazov et al. | |
| 2010/0185142 A1 | 7/2010 | Kamen et al. | |
| 2010/0185175 A1 | 7/2010 | Kamen et al. | |
| 2010/0198183 A1 | 8/2010 | Lanigan et al. | |
| 2010/0217192 A1 | 8/2010 | Moberg et al. | |
| 2010/0217193 A1 | 8/2010 | Moberg et al. | |
| 2010/0241065 A1 | 9/2010 | Moberg et al. | |
| 2010/0256561 A1 | 10/2010 | Gillespie, Jr. et al. | |
| 2010/0256565 A1 | 10/2010 | Mernoee et al. | |
| 2010/0274192 A1 | 10/2010 | Mernoe | |
| 2010/0331824 A1 | 12/2010 | Moberg et al. | |
| 2011/0004188 A1 | 1/2011 | Shekalim | |
| 2011/0021993 A1* | 1/2011 | Bar-Haim | A61M 5/16854 |
| | | | 604/153 |
| 2011/0030845 A1 | 2/2011 | Chong et al. | |
| 2011/0040247 A1 | 2/2011 | Mandro et al. | |
| 2011/0047499 A1 | 2/2011 | Mandro et al. | |
| 2011/0077493 A1 | 3/2011 | Shadforth et al. | |
| 2011/0098676 A1 | 4/2011 | Chiang et al. | |
| 2011/0112504 A1 | 5/2011 | Causey et al. | |
| 2011/0118662 A1 | 5/2011 | Mhatre et al. | |
| 2011/0144586 A1 | 6/2011 | Michaud et al. | |
| 2011/0144616 A1 | 6/2011 | Michaud et al. | |
| 2011/0152770 A1 | 6/2011 | Diperna et al. | |
| 2011/0152824 A1 | 6/2011 | Diperna et al. | |
| 2011/0154237 A1 | 6/2011 | Bush et al. | |
| 2011/0166544 A1 | 7/2011 | Verhoef et al. | |
| 2011/0178461 A1 | 7/2011 | Chong et al. | |
| 2011/0184653 A1 | 7/2011 | Ray et al. | |
| 2011/0190614 A1 | 8/2011 | Brister et al. | |
| 2011/0190694 A1 | 8/2011 | Lanier, Jr. et al. | |
| 2011/0192478 A1 | 8/2011 | Chong et al. | |
| 2011/0205065 A1 | 8/2011 | Strachan et al. | |
| 2011/0213306 A1 | 9/2011 | Hanson et al. | |
| 2011/0213329 A1 | 9/2011 | Yodfat et al. | |
| 2011/0319813 A1 | 12/2011 | Kamen | |
| 2011/0319862 A1 | 12/2011 | Friedman et al. | |
| 2012/0029433 A1 | 2/2012 | Michaud et al. | |
| 2012/0029468 A1 | 2/2012 | Diperna | |
| 2012/0030610 A1 | 2/2012 | Diperna et al. | |

(56)  References Cited

U.S. PATENT DOCUMENTS

| | | |
|---|---|---|
| 2012/0091813 A1 | 4/2012 | Spurlin et al. |
| 2012/0238851 A1 | 9/2012 | Kamen |
| 2013/0012917 A1 | 1/2013 | Miller et al. |
| 2013/0015980 A1 | 1/2013 | Evans |
| 2013/0053816 A1 | 2/2013 | DiPerna et al. |
| 2013/0159456 A1 | 6/2013 | Daoud et al. |
| 2013/0172710 A1 | 7/2013 | Mears |
| 2013/0283196 A1 | 10/2013 | Farnan |
| 2013/0324928 A1 | 12/2013 | Kruse |
| 2013/0331790 A1 | 12/2013 | Brown et al. |
| 2014/0054883 A1 | 2/2014 | Lanigan et al. |
| 2014/0113553 A1 | 4/2014 | Brukalo |
| 2014/0207065 A1 | 7/2014 | Yavorsky |
| 2015/0011970 A1 | 1/2015 | Kamen |
| 2015/0119805 A1 | 4/2015 | Blomquist |
| 2015/0317437 A1 | 11/2015 | Daoud et al. |
| 2016/0136357 A1 | 5/2016 | Yang |
| 2016/0157759 A1 | 6/2016 | Yang |
| 2016/0157765 A1 | 6/2016 | Zhu |
| 2016/0158436 A1 | 6/2016 | Yang |
| 2016/0199572 A1 | 7/2016 | Yang |
| 2016/0271325 A1 | 9/2016 | Farnan et al. |
| 2016/0339172 A1 | 11/2016 | Michaud |
| 2017/0049957 A1 | 2/2017 | Michaud |
| 2017/0056582 A1 | 3/2017 | Niklaus |
| 2017/0266381 A1 | 9/2017 | Bryant, Jr. |
| 2018/0071454 A1 | 3/2018 | Betts et al. |
| 2018/0137252 A1 | 5/2018 | Mairs |
| 2018/0137938 A1 | 5/2018 | Vaddiraju |
| 2018/0193555 A1 | 7/2018 | Michaud et al. |
| 2019/0167902 A1 | 6/2019 | Kamen |
| 2019/0240398 A1 | 8/2019 | Seitz et al. |
| 2019/0255248 A1 | 8/2019 | Michaud |
| 2019/0321545 A1 | 10/2019 | Saint |
| 2019/0321546 A1 | 10/2019 | Michaud et al. |
| 2019/0321552 A1 | 10/2019 | DiPerna et al. |
| 2019/0351134 A1 | 11/2019 | Cook et al. |
| 2020/0009319 A1 | 1/2020 | Ludolph |
| 2020/0009320 A1 | 1/2020 | Ludolph |

FOREIGN PATENT DOCUMENTS

| | | | |
|---|---|---|---|
| EP | 2410448 A2 | 1/2012 | |
| WO | WO-2004056412 A2 | 7/2004 | |
| WO | WO-2007065944 A1 | 6/2007 | |
| WO | WO-2008103175 A1 | 8/2008 | |
| WO | WO-2008144693 A1 | 11/2008 | |
| WO | WO-2008144695 A1 | 11/2008 | |
| WO | WO-2008144697 A1 | 11/2008 | |
| WO | WO-2008144698 A1 | 11/2008 | |
| WO | WO-2009013736 A1 | 1/2009 | |
| WO | WO-2009016636 A2 | 2/2009 | |
| WO | WO-2009098648 A2 | 8/2009 | |
| WO | WO-2009124133 A2 | 10/2009 | |
| WO | WO-2011014704 A2 | 2/2011 | |
| WO | WO-2014029416 A1 * | 2/2014 | ........ A61M 39/1011 |

OTHER PUBLICATIONS

Application and File History for U.S. Appl. No. 15/987,432, filed May 23, 2018, inventors Michaud et al.
International Preliminary Report on Patentability for Application No. PCT/US2016/033054, mailed on Nov. 30, 2017, 6 pages.
International Search Report and Written Opinion for Application No. PCT/US2016/033054, mailed on Sep. 1, 2016, 13 pages.

* cited by examiner

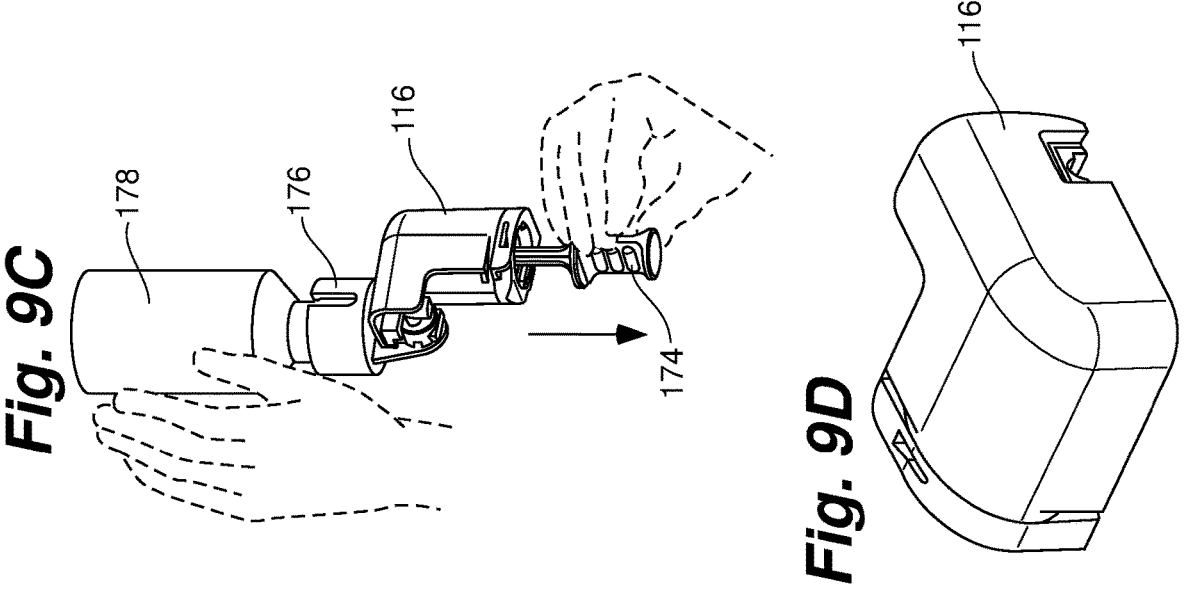
Fig. 9C
Fig. 9D
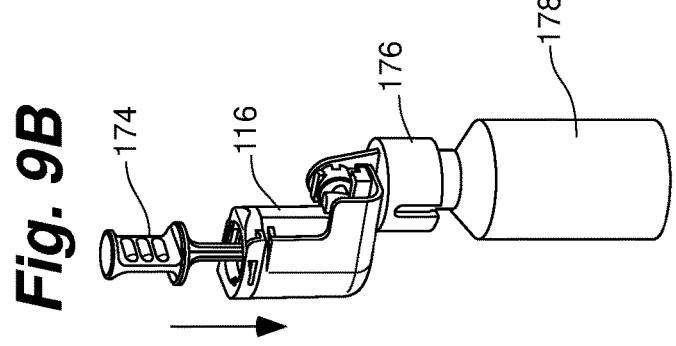
Fig. 9B
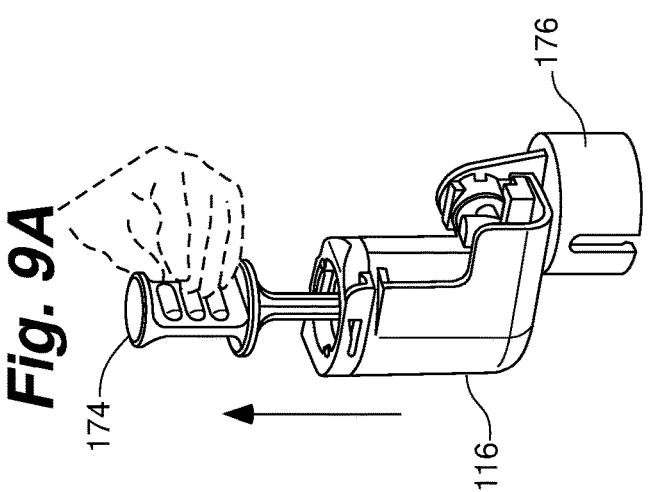
Fig. 9A

*Fig. 10C*
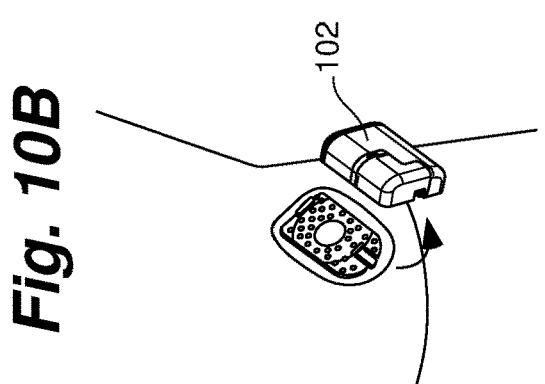
102
*Fig. 10B*
102
*Fig. 10E*
102
180
*Fig. 10A*
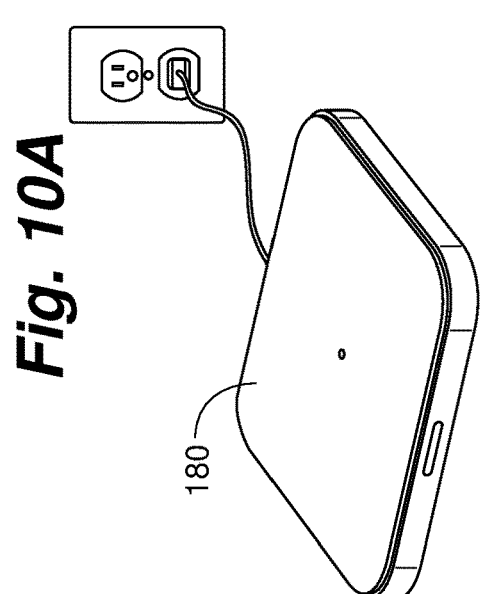
180
*Fig. 10D*
182
180

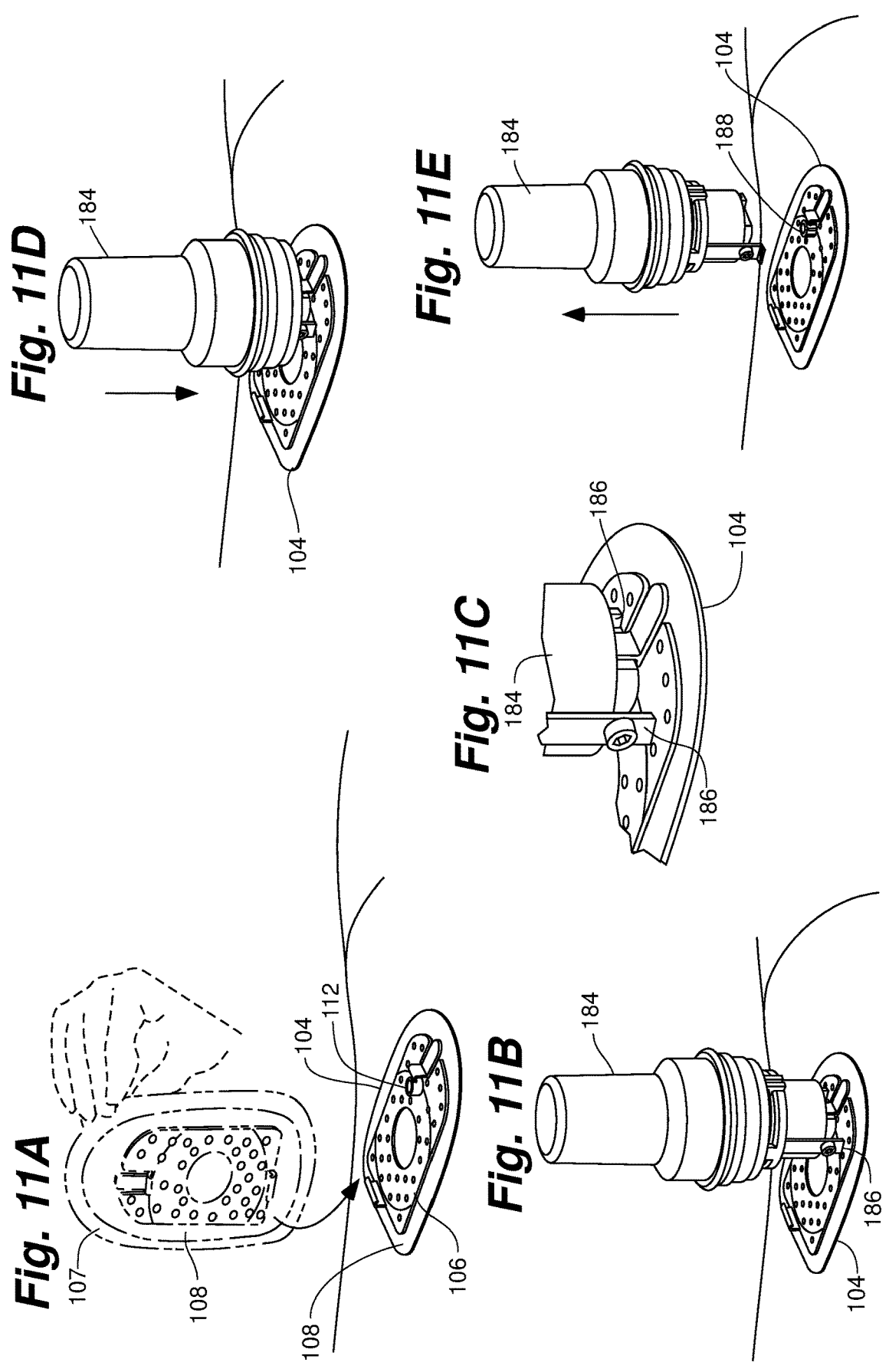

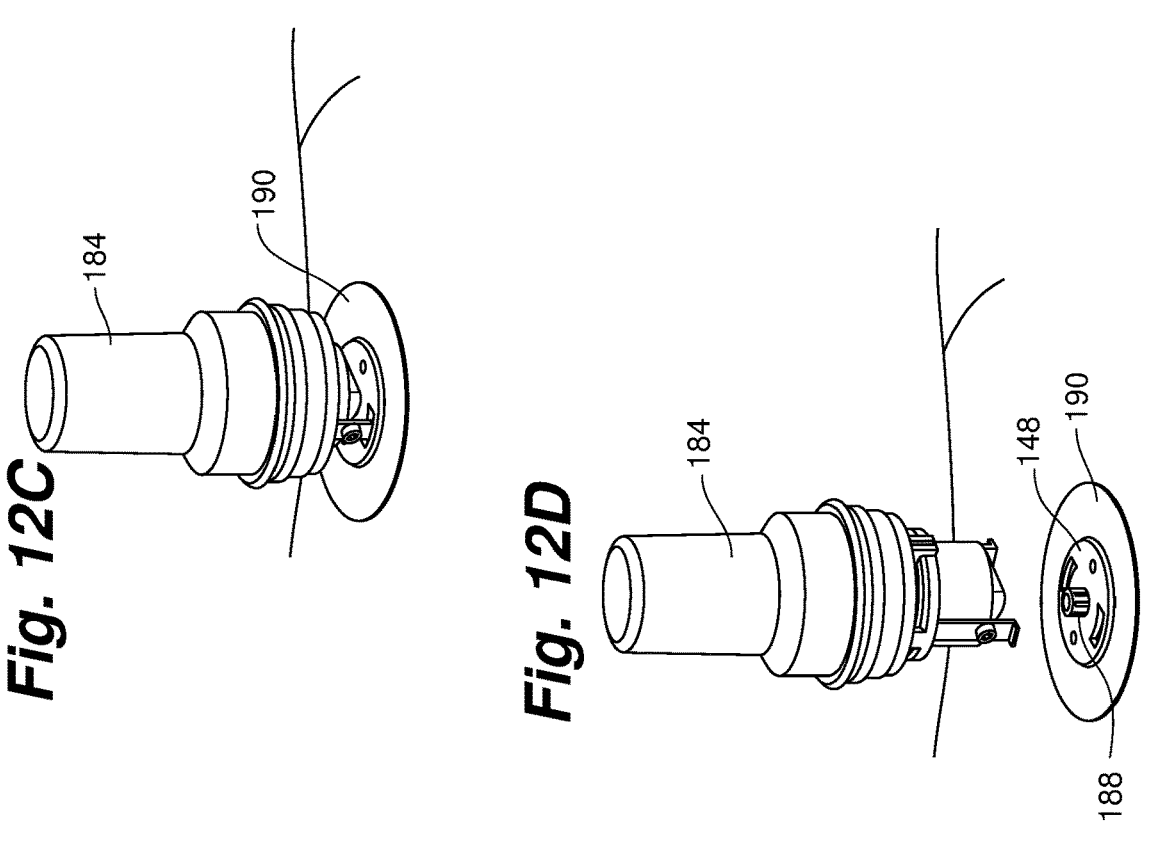
*Fig. 12C*
*Fig. 12A*
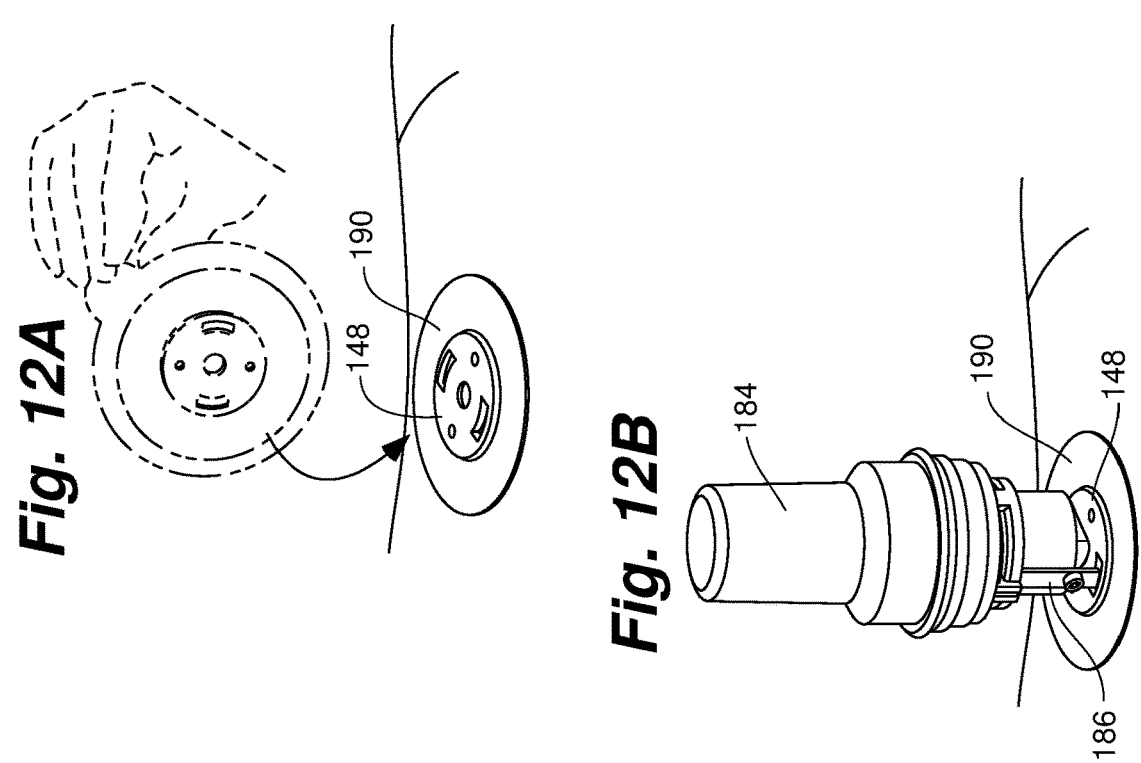
*Fig. 12D*
*Fig. 12B*

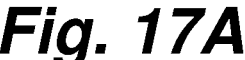
*Fig. 17A*
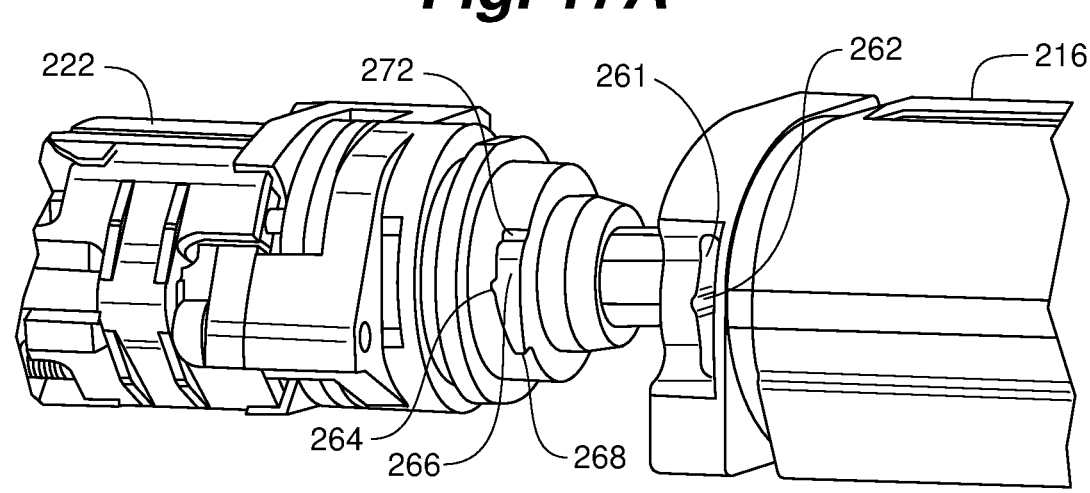
*Fig. 17B*
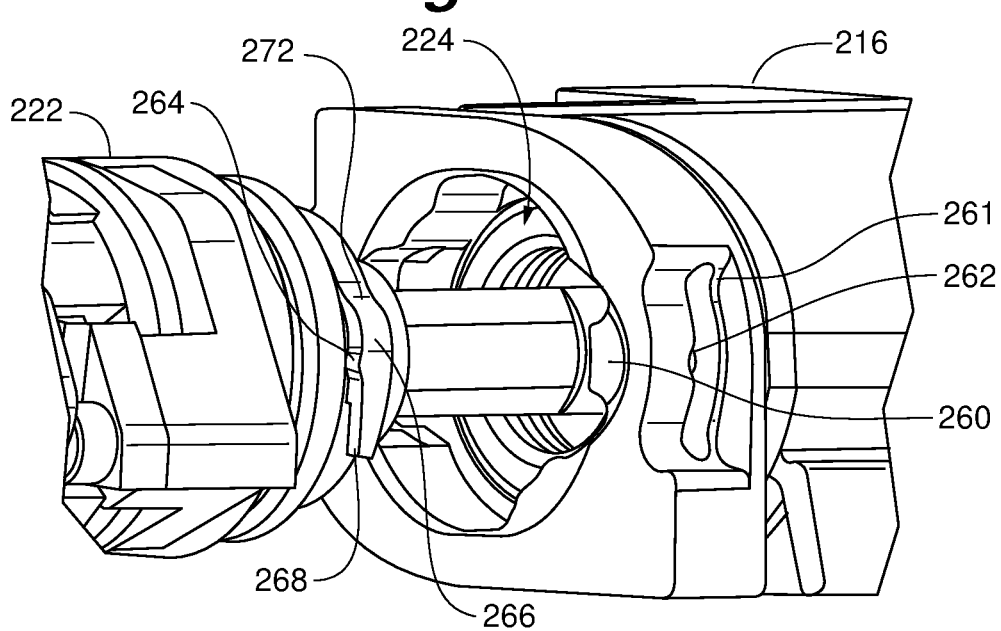

PATCH PUMP CARTRIDGE ATTACHMENT

RELATED APPLICATION

This application is a continuation of application Ser. No. 15/987,432 filed May 23, 2018, now U.S. Pat. No. 10,864, 318 issued Dec. 15, 2020; which is a continuation of application Ser. No. 15/158,125 filed May 18, 2016, now U.S. Pat. No. 9,993,595 issued Jun. 12, 2018, which claims the benefit of U.S. Provisional Application No. 62/163,158 filed May 18, 2015, each of which is hereby incorporated herein in its entirety by reference.

FIELD OF THE INVENTION

The present invention relates to medical pumps for delivering medicament to a patient and, more specifically, to a user-wearable insulin patch pump for delivering insulin to a patient.

BACKGROUND OF THE INVENTION

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. Patent Application Publication No. 2013/0053816, U.S. Pat. Nos. 8,573,027, 8,986,253, U.S. Patent Application Publication No. 2013/0324928, U.S. Patent Application Publication No. 2013/0331790 and U.S. Pat. No. 8,287,495, each of which is hereby incorporated herein by reference in its entirety.

One type of pump that has been developed is a patch pump, or micro pump. Patch pumps are small pumps, typically ambulatory, that are carried directly on the skin under the user's clothing. Many such pumps are situated directly on the injection site such that no tubing is required to deliver the insulin or other medicament to the patient. Other patch pumps can be positioned on the user's body with a short length of tubing extending to a nearby infusion site. Patch pumps typically are at least in part disposable, meant to be worn for a day or two and then discarded for a new patch pump.

BRIEF DESCRIPTION OF THE DRAWINGS

Subject matter hereof may be more completely understood in consideration of the following detailed description of various embodiments in connection with the accompanying figures, in which:

FIGS. 9A-9D depict a procedure for filling a cartridge of a patch pump system according to an embodiment of the present invention.

FIGS. 10A-10E depict a procedure for inductively charging the battery of a patch pump system according to an embodiment of the present invention.

FIGS. 11A-11E depict a procedure for inserting a cannula into the skin of a user of a patch pump system according to an embodiment of the present invention.

FIGS. 12A-12D depict a procedure for inserting a cannula into the skin of a user of a patch pump system according to an embodiment of the present invention.

FIGS. 15-16, 17A-17B, 18A-18C and 19 are schematic representations of a cartridge and drive mechanism of a patch pump system according to an embodiment of the present invention.

Figures 1A, 1B:
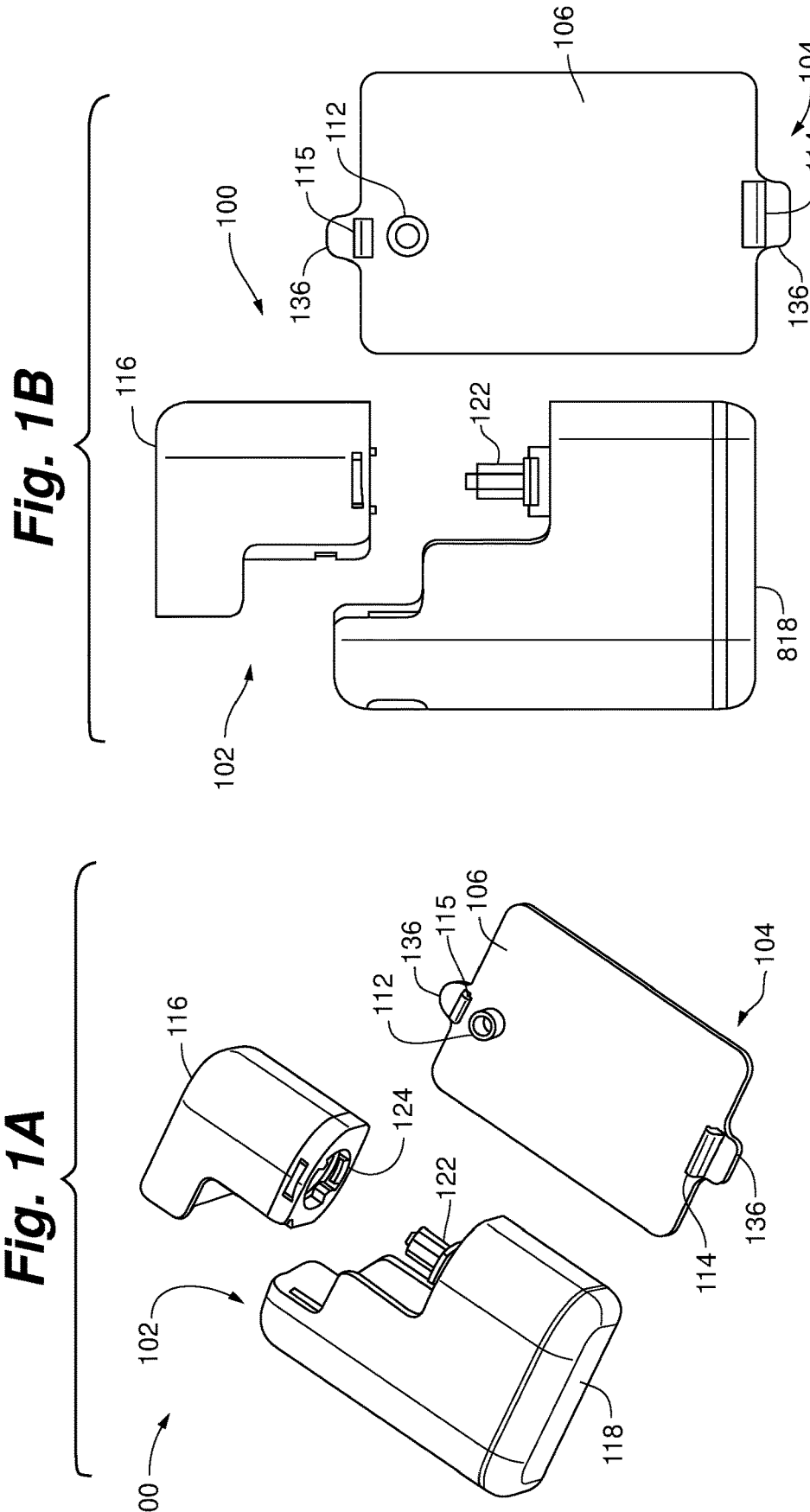
FIGS. 1A-1F are views of portions of a patch pump system according to an embodiment of the present invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

SUMMARY

A user-wearable patch pump system for delivery of insulin or other medicament can include a patch pump having a reusable drive unit and a replaceable and/or refillable cartridge. The cartridge can selectively attach to and be detached from the drive unit. The cartridge can initially be inserted onto the drive unit in a first orientation at an angle to the drive unit and then be rotated to align the cartridge with the drive unit and lock the cartridge in place on the drive unit to form the patch pump.

In some embodiments a user-wearable infusion pump system includes a pump having a disposable cartridge and a drive unit. The disposable cartridge can be configured to contain a medicament and include a cartridge housing having a front surface and a rear surface and a coupling recess defined in a bottom surface of the cartridge housing. The drive unit can be configured to cause medicament in the cartridge to be delivered to a user wearing the pump and include a drive unit housing having a front surface and a rear surface and a drive mechanism having a drive end extending from the drive unit. The coupling recess in the cartridge can be configured to be inserted onto the drive end of the drive mechanism with the cartridge in a first orientation with respect to the drive unit and the cartridge can be configured to then be rotated with respect to the drive unit in a first direction with the drive end in the coupling recess to lock the cartridge onto the drive unit in a second orientation with the front surface of the cartridge aligned generally parallel with the front surface of the drive unit. In various embodiments, the angle between the cartridge and drive unit can be between about 30 degrees and about 150 degrees, including for example, a generally perpendicular (about 90 degree angle) and about a 60 degree angle.

In some embodiments, the cartridge includes a pair of flanges on opposing sides of the coupling recess each adjacent a respective slot and the drive end includes a pair of threads on opposing sides of the drive end. The flanges, slots and threads cooperate to lock the cartridge onto the drive unit in the second orientation with each thread seating in a respective one of the slots. The flanges can be positioned axially proximally in the coupling recess with respect to the slots; the cartridge is rotated from the first orientation to the second orientation by inserting the cartridge onto the drive end to axially advance the threads past the flanges to align the threads with the slots and by rotating the cartridge to seat the threads in the slots.

In such embodiments, flanges in coupling recess serve the dual purpose of ensuring proper angular orientation and axial insertion depth of the cartridge for the connection, in addition to aiding in retaining the cartridge on the drive unit once it is connected. If the threads on the drive end and the flanges in the coupling recess are positioned such that the threads are rotationally aligned with the flanges, the flanges will prevent the threads from being axially advanced past the flanges, requiring a proper angular orientation of the cartridge with respect to the drive unit to reach the proper insertion depth. In addition, if the cartridge is rotated for the connection prior to reaching that proper axial insertion depth, the flanges in the coupling recess instead will be axially aligned with the threads on the drive unit, such that the threads will inhibit rotation of the cartridge by abutting the flanges, thus preventing connection of the cartridge to the drive unit. In some embodiments, the threads and flanges can include corresponding concave and convex or otherwise mating surfaces, respectively, that interface with each other to prevent excess wear on the components due to such interactions.

In such embodiments, the slots in the cartridge recess and the corresponding threads on the drive mechanism can have additional complementary features to ensure a strong and reliable coupling of the cartridge to the drive unit. The threads can, for instance, include detent projections that nest into detent grooves in the slots when the cartridge has been rotated to seat the threads in the slots and provide tactile and even audible feedback to the user to confirm a secure and proper connection. These detents help prevent the cartridge from freely rotating with respect to the drive unit while still enabling the cartridge to be rotated in the opposite direction to disconnect the cartridge from the drive unit if a required amount of rotational force is applied. The threads can also increase in width from a leading edge of the threads that first enters the slots as the cartridge is rotated to provide a secure compression fit between the threads and the slots.

The above summary is not intended to describe each illustrated embodiment or every implementation of the subject matter hereof. The figures and the detailed description that follow more particularly exemplify various embodiments.

DETAILED DESCRIPTION

FIGS. 1A-1F depict a patch pump 100 including a pump 102 and an attachment portion 104 according to an embodiment of the invention. Patch pump 100 does not include a built-in display or user interface, and is therefore primarily remote controlled. Retention frame 106 of attachment portion 104 includes an insertion portion 112 through which a disposable needle can be inserted to penetrate a sealing membrane and insert a cannula for medicament delivery. Reusable drive unit 118 of pump includes a drive mechanism 122 that mates with a recess 124 in disposable cartridge 116 to attach the cartridge 116 to the drive unit 118 and provide for delivery of medicament such as insulin from the cartridge 116 to a user through the cannula.

Figure 1C:
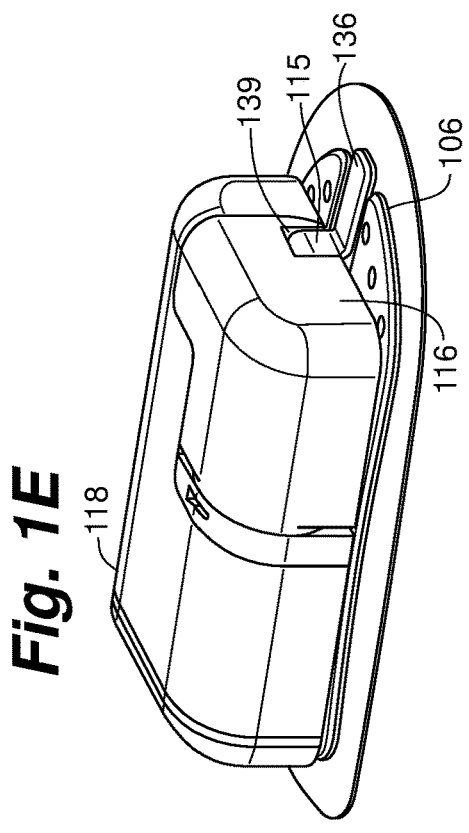
Figure 1E:
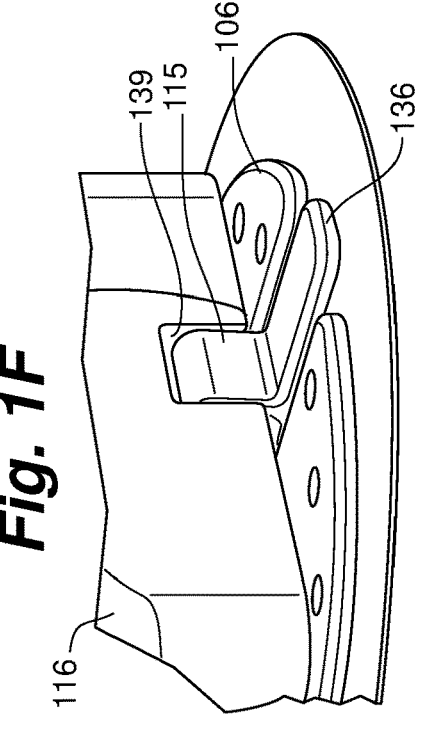
Figure 1D:
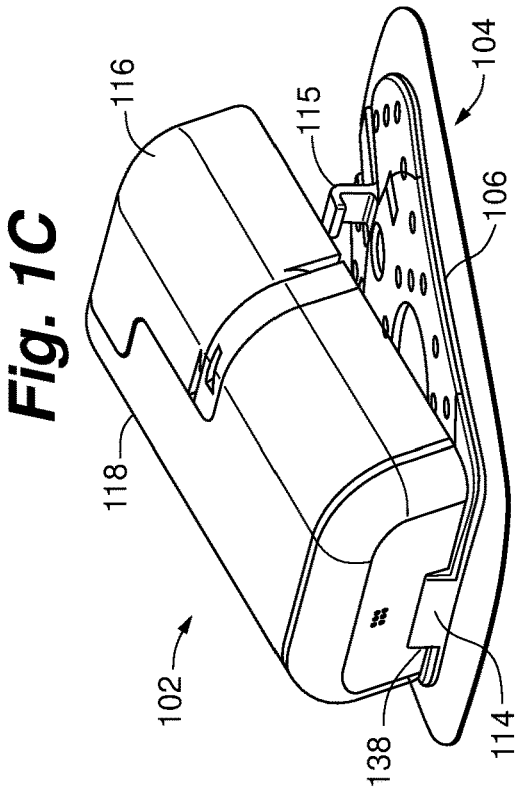
Figure 1F:
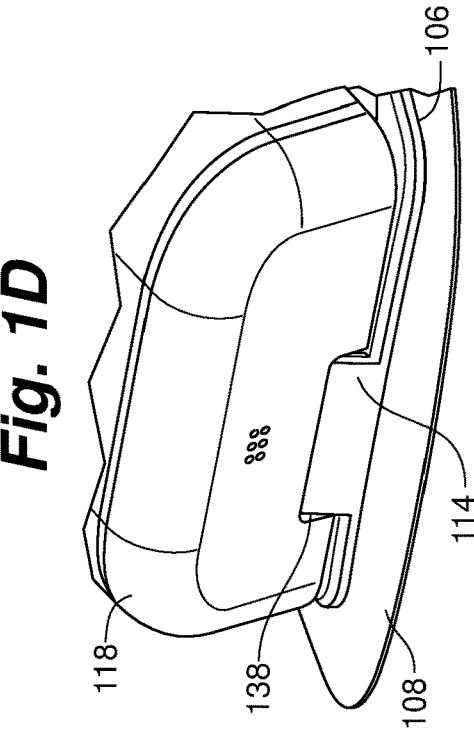

Retention frame 106 in this embodiment includes a hook portion 114 adjacent one end of the frame and a snap portion 115 adjacent an opposing end of the frame. To mate the pump 102 with the corresponding attachment portion 104, initially hook portion 114 on retention frame 106 is inserted, or hooked, into a recess 138 in the drive unit 118, as shown in FIGS. 1C and 1D. To complete the insertion and mating process, the pump 102 is pivoted downwardly about the hook portion 114 to mate a recess 139 in cartridge 116 with snap portion 115, as shown in FIGS. 1E and 1F. Snap portion 115 can be flexible and resilient such that when the cartridge 116 is mated with the snap portion 115, the snap portion 115 is initially pushed away from the pump 102 and then snaps into place when aligned with the recess 139 to cause an audible clicking or snapping sound that provides an indication to the user that the pump 102 is properly mated to the attachment portion 106. Pump 102 can be released from attachment portion 104 to, for example, enable a user to exchange the cartridge, with one or more tabs 136, which can be depressed to cause one or both of hook portion 114 and snap portion 115 to withdraw from its corresponding recess in pump 102.

Figures 2A, 2B, 2C:
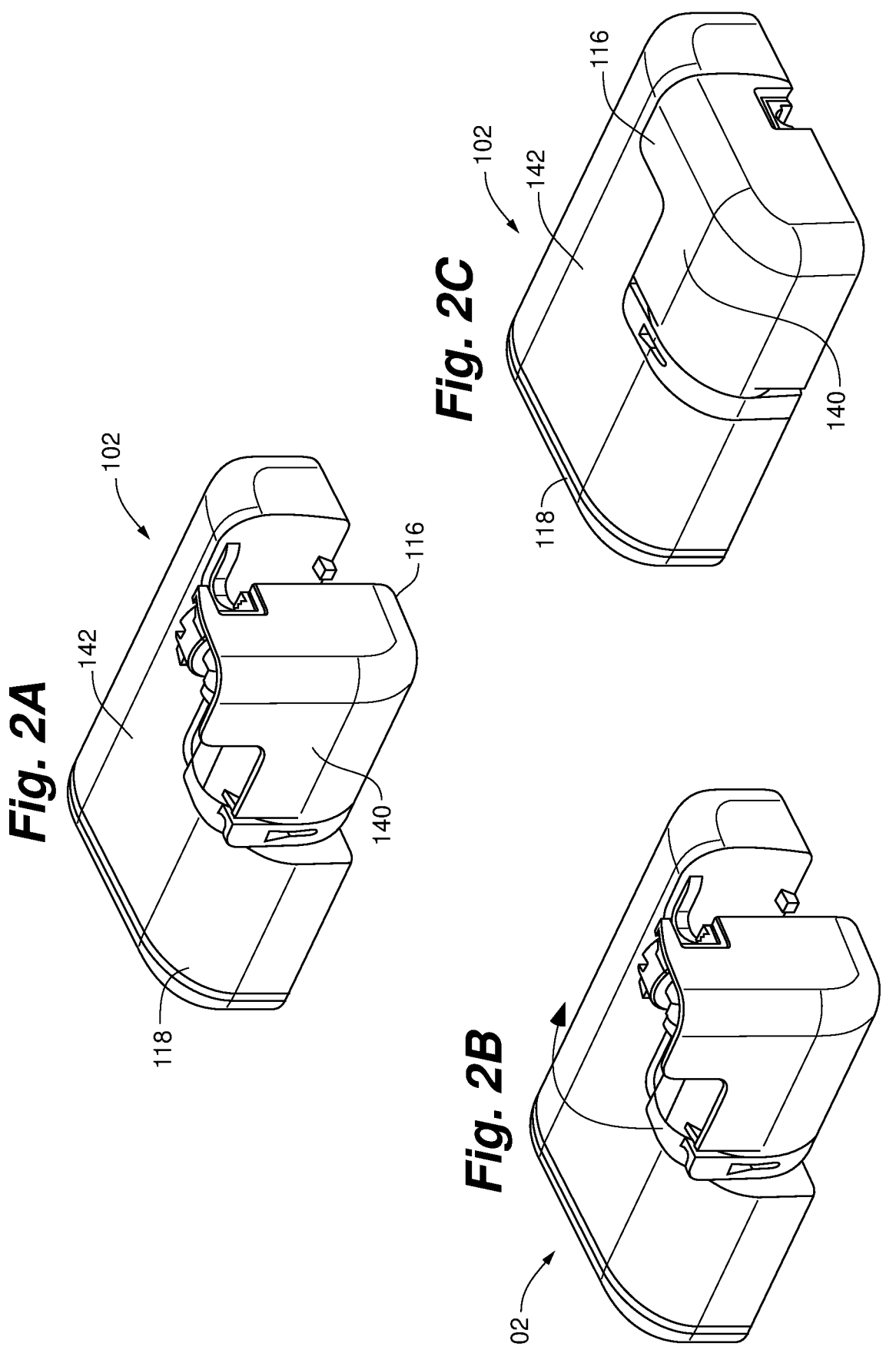
FIGS. 2A-2C depict a cartridge being attached to a drive unit of a patch pump system according to an embodiment of the present invention.

In one embodiment, and as shown in FIGS. 2A-2C, cartridge 116 of pump 102 can attach to drive unit 118 with a quarter turn attachment. Recess 124 of cartridge 116 can be configured to initially attach to drive mechanism 122 of drive unit 118 such that an outer front housing surface 840 of the cartridge 116 is offset from an outer front housing surface 142 of the drive unit 818 at an angle of, e.g., about 90 degrees (generally perpendicular). The cartridge 116 can then be rotated toward the drive unit 118 a quarter-turn to align the outer surface 140 of the cartridge 116 generally parallel with the outer surface 142 of the drive unit 118 and secure the cartridge 116 on the drive unit 118. In one embodiment, the engagement of the cartridge 116 to the drive unit 118 made by this rotation can cause an audible clicking sound that provides an auditory indication to the user that the cartridge is properly attached by the use of, e.g., detent projections and grooves described herein. Such a feature can alternatively or additionally provide a tactile indication to the user that the cartridge is properly attached.

FIGS. 3A-3D depict further detail regarding such a cartridge 116 attachment. In these figures, a housing of the drive unit 118 is not shown and only the drive mechanism 122 is depicted for sake of clarity. Cartridge 116 can include a pair of opposing flanges 160 adjacent recess 124, which can be comprised of a flexible material. Cartridge 116 can also include one or more detent projections 162, with two such detent projections 162 depicted in this embodiment. The drive mechanism 122 can include one or more detent grooves 164 corresponding to the detent projections 162 on the cartridge, although alternatively the drive mechanism 122 could include the projections and the cartridge 116 could include the grooves. The drive mechanism 122 can also include one or more partial turn threads 166, with this embodiment including a pair of quarter-turn threads on opposing sides of the mechanism.

Figure 3A:
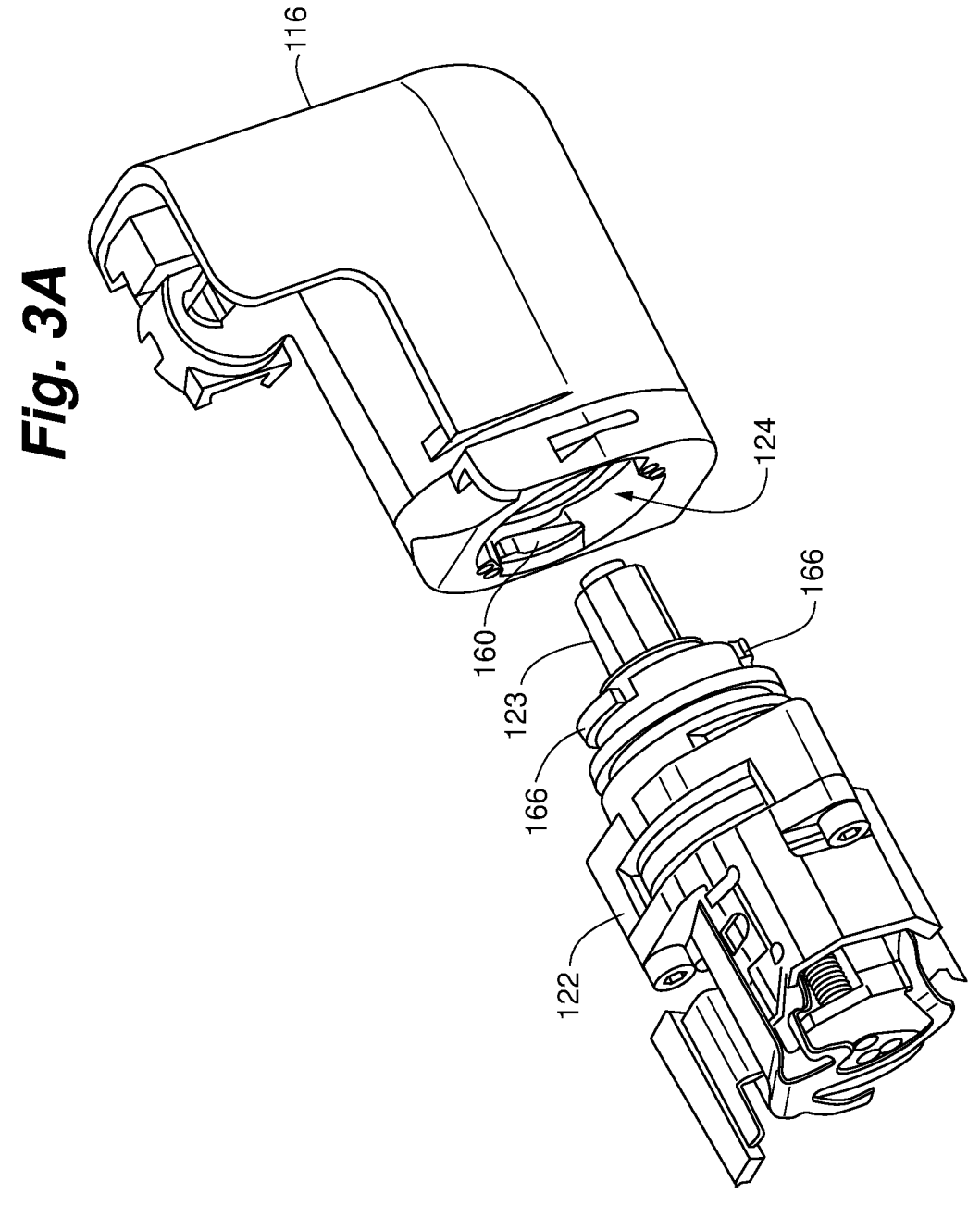
FIGS. 3A-3D are schematic representations of a cartridge and drive mechanism of a patch pump system according to an embodiment of the present invention.
Figure 3B:
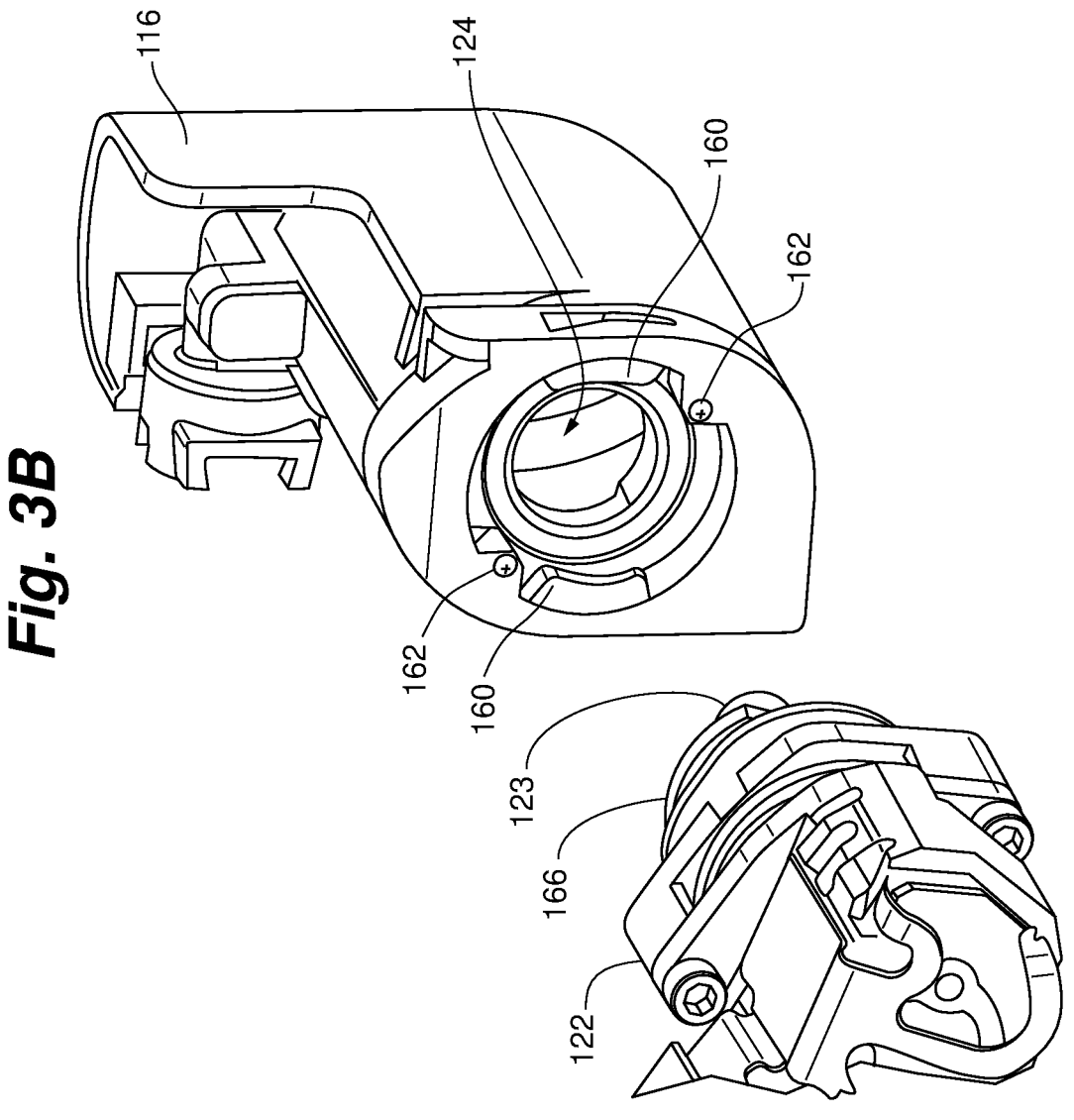
Figure 3C:
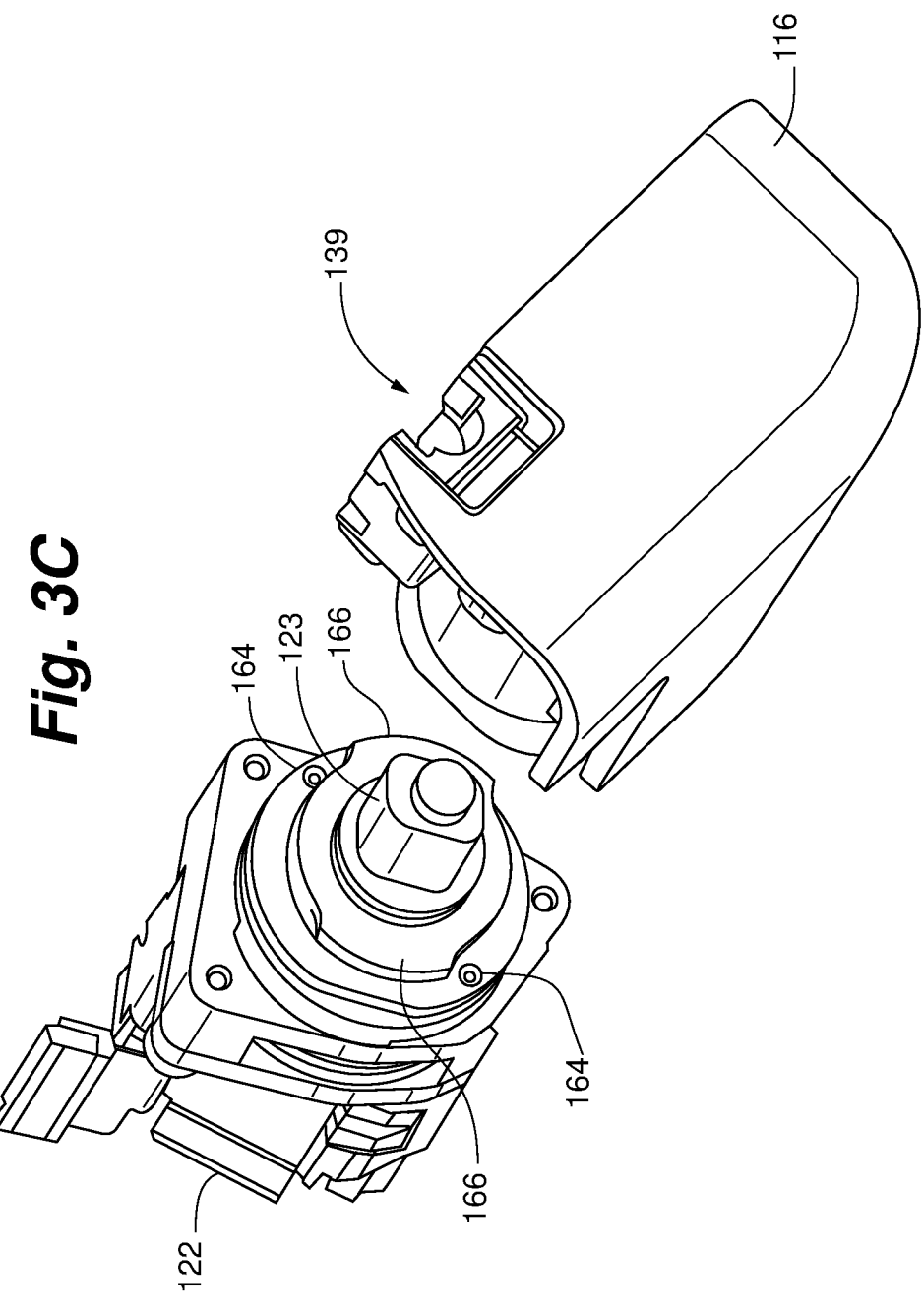
Figure 3D:
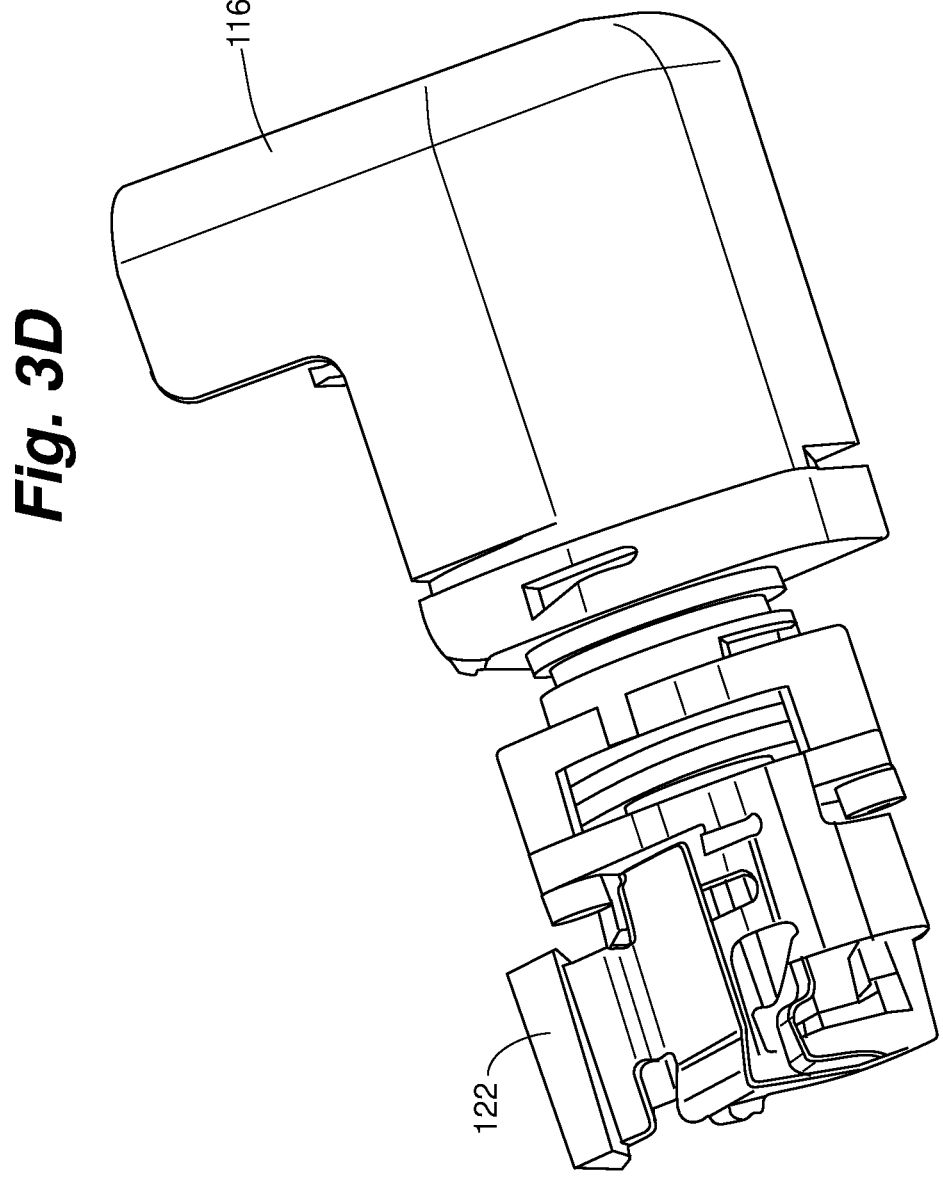

To engage the cartridge 116 with the drive mechanism 122, the drive end 123 of the drive mechanism 122 can be inserted into the recess 124 of the cartridge 116 with the quarter-turn threads 166 of the drive mechanism 122 offset from the flanges 160 of the cartridge 116, as shown in FIG. 3A. This enables the quarter-turn threads 166 to be inserted into the recess 124 past the flanges 160 so that when the cartridge 116 is rotated into alignment with the drive unit 118, the quarter-turn threads 166 and the flanges 160 align with and axially abut and/or align with each other to prevent the threads 166 from being withdrawn back through the recess 124. Therefore, interference between the quarter-turn threads 166 and the flanges 160 will prevent the cartridge 116 from being pulled directly off of the drive mechanism 122 in this alignment, keeping the cartridge rigidly affixed to the drive mechanism 122. In addition, the detent projections 162 on the cartridge 116 nest into the detent grooves 164 in the drive mechanism 122 at the completion of the quarter-turn rotation. This prevents the cartridge 116 from freely rotating out of alignment with the drive unit 118, and correspondingly the flanges 160 from freely rotating out of alignment with the quarter-turn threads 166, while still enabling such rotation if a required amount of rotational force is applied. Although described as a "quarter-turn," i.e., about a 90 degree rotation, it should be understood that a wide variety of rotational angles can be employed as discussed herein.

In one embodiment, the pump 102 is a syringe pump in which a plunger is incrementally advanced to dispense insulin or other medicament. Such pumps typically require a cap, such as a screw cap, to be disposed on the pump at an end of the syringe to prevent unintended dispensing of insulin. In the rotational attachment embodiment of the cartridge 116 described above, the rotation of the cartridge on attachment enables the cartridge to essentially function as a cartridge and an integrated screw cap to prevent unintended dispensing of insulin, thereby removing the need for the additional component of the screw cap.

Figures 4A, 4B, 5A, 5B:
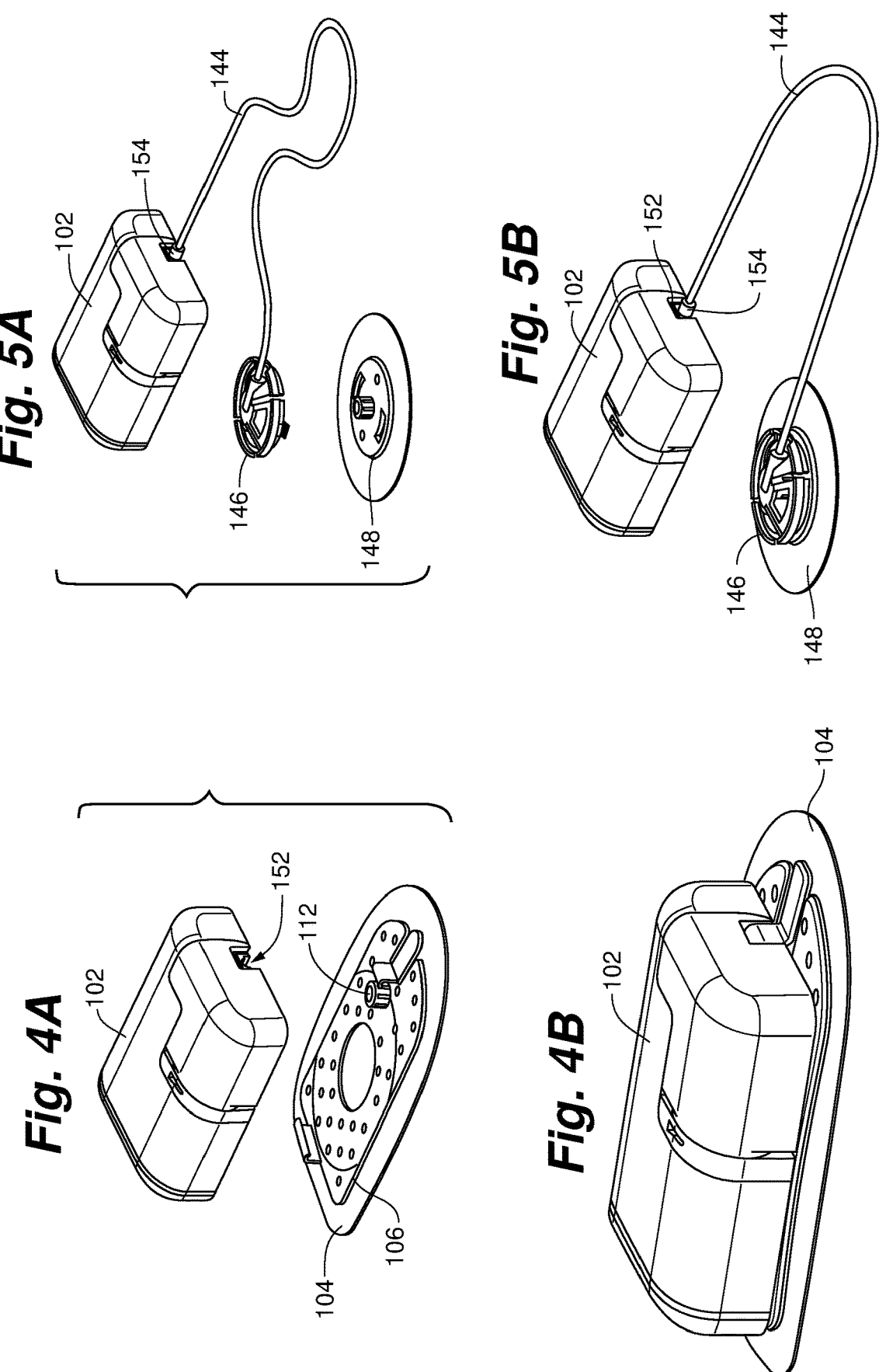
FIGS. 4A-4B, 5A-5B and 6A-6B depict alternate uses of a patch pump according to an embodiment of the present inventions.
Figure 6B:
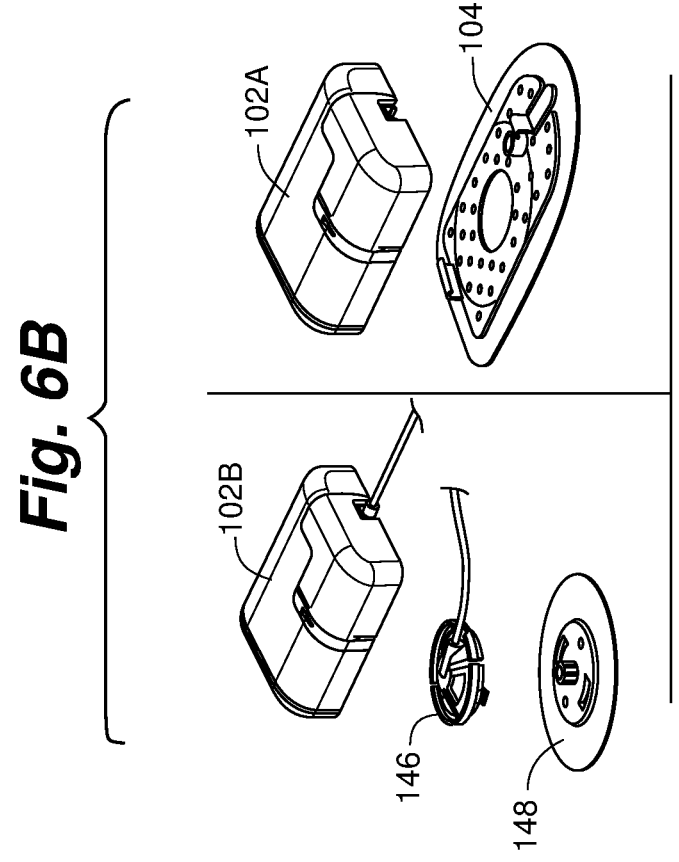
Figure 6A:
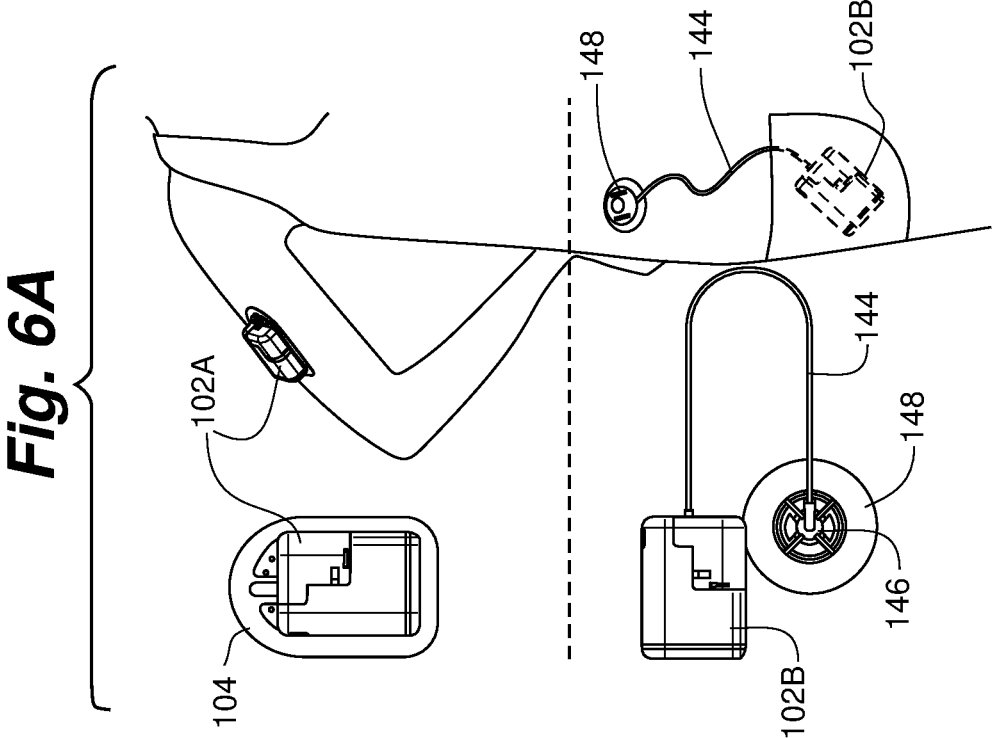

FIGS. 4A-4B and FIGS. 5A-5B depict that in some embodiments a pump such as pump 802 can be interchangeably used either with attachment portion 104 to deliver medicament to an infusion site beneath the pump 102 or with tubing 144 and a connector 146 to deliver medicament through an infusion site connector 148 displaced from the pump 102. Pump 102 can include a recess 139, more clearly shown in FIG. 3C, that can include one or both of an opening (not pictured) configured to align with an insertion site 112 in the retention frame 106 and an opening 152 configured to connect to an end connector 154 of tubing 144. Recess 139 can also aid in attaching pump 102 to the retention frame 106 as discussed with respect to FIGS. 1C-1F. The pump 102 can therefore alternatively be used either with that attachment portion 104 as shown in FIG. 4 or the tubing 144 and infusion site connector 148 as shown in FIG. 5 according to user preference. FIGS. 6A and 6B further illustrate these alternative uses. Pump 102A is depicted as being used with an attachment portion 104 carried directly on the user, whereas pump 102B is depicted utilizing tubing 144 having an end connector 146 connecting to an infusion site connector 148 attached to the user with the pump 102B carried in a separate location, such as in the user's pocket.

Figure 7B:
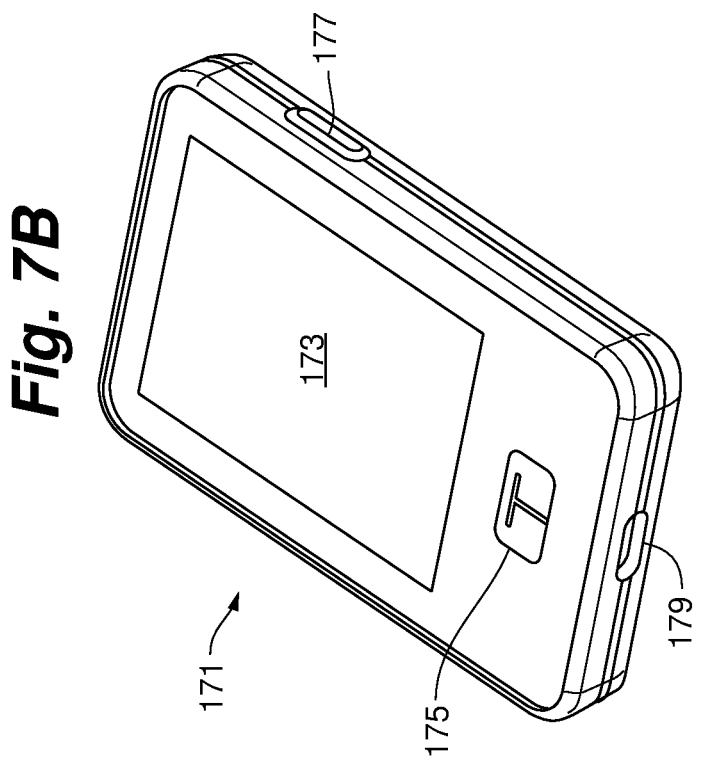
FIGS. 7A-7C depicts remote control devices for a patch pump system according to embodiments of the present invention.
Figure 7A:
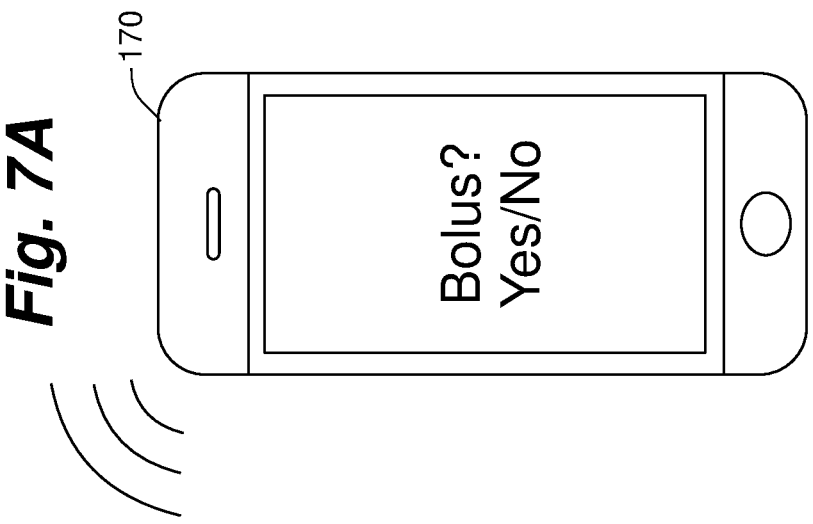
Figure 7C:
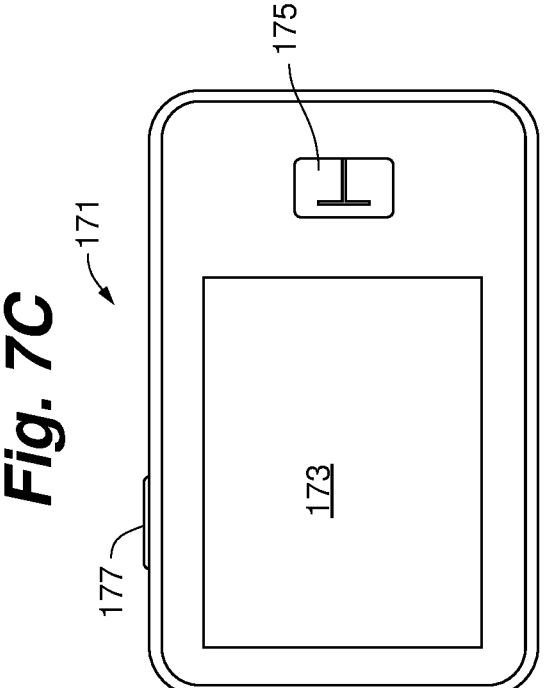

FIGS. 7A-7C depict a remote control devices that can be used to control delivery of medicament and transfer data with a patch pump via Bluetooth, Bluetooth low energy, mobile or Wi-Fi communication, for example, according to embodiments of the present invention. Such a remote control could include, for example, a dedicated remote controller 171 as shown in FIGS. 7B-7C, a mobile communication device 170 such as a smartphone as shown in FIG. 7A, a wearable electronic watch or electronic health or fitness monitor or a personal digital assistant (PDA), etc. or a tablet, laptop or personal computer.

Referring to FIGS. 7B-7C, a dedicated remote controller 171 according to embodiments of the invention can include a touchscreen display 173. Touchscreen 173 can, in various embodiments, include a color display and be a capacitive touchscreen, resistive touchscreen, or the like and can be single touch or multi-touch touchscreen. Dedicated remote controller 171 can further include one or more of a touch-sensitive button 175, a push button 177 and a port 179. In some embodiments, touch-sensitive button 175 can be configured to return the controller 171 to a home screen from another menu screen any time the button 175 is touched and the push button 177 can be configured to wake the device from a sleep or off mode and activate the display 173 any time the button 177 is pressed. In other embodiments, these functions can be reversed or both functions can be accomplished with a single button depending on the current state of the device. Port 179 can be any type of port known in the art for data transfer and charging of a rechargeable battery in the controller 171, such as, for example, a USB port. Controller 171 can additionally include one or more of a speaker/microphone, vibrator and/or light, such as an LED light, for providing alerts, alarms, notifications, etc.

Figure 8:
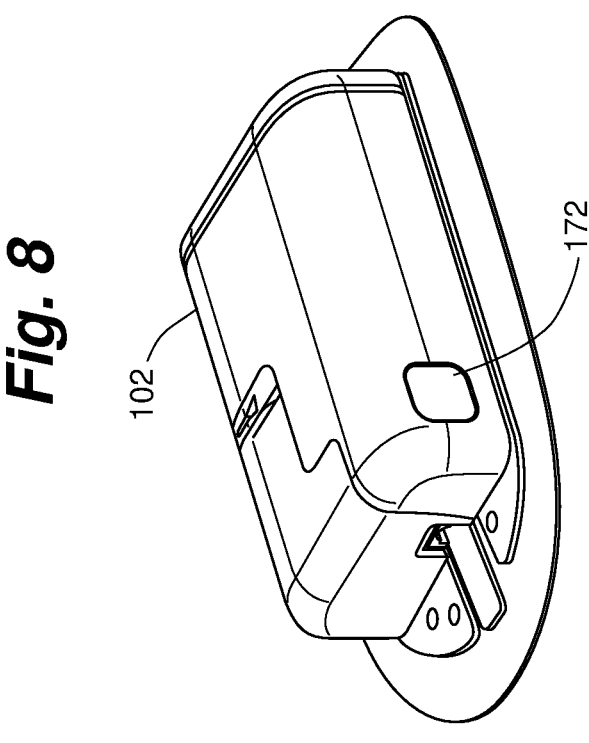
FIG. 8 depicts a patch pump system according to an embodiment of the present invention.

FIG. 8 depicts a bolus button 172 located on the pump 102 that can also be used to initiate delivery of medicament with pump 102. Because the depicted patch pump does not itself include a display or user interface, information and feedback regarding dosing initiated with the bolus button 172 can be communicated to and displayed on the remote control device 170.

In some embodiments, patch pumps as described herein can interface with a glucose meter, such as a blood glucose meter (BGM) or a continuous glucose monitor (CGM), the latter category of which provides a substantially continuous estimated glucose level through a transcutaneous sensor that measures analytes, such as glucose, in the patient's interstitial fluid rather than the patient's blood. Patch pump system can use data obtained from a glucose meter such as a CGM to adjust therapy with patch pump either automatically, such as in a closed-loop or semi-closed loop "artificial pancreas" system, or by providing such data for user review via a remote control device 170, 171. The data may be transmitted from the CGM to the patch pump and/or remote controller via a wireless transmitter, such as a near field communication (NFC) radio frequency (RF) transmitter or a transmitter operating according to a "Wi-Fi" or Bluetooth® protocol or the like, or the data may be transmitted via a wire connector. Further detail regarding CGM systems and definitions of related terms can be found in, e.g., U.S. Pat. Nos. 8,311,749, 7,711,402 and 7,497,827, each of which is hereby incorporated by reference in its entirety.

FIGS. 9A-9D depict one example of a procedure or method for filling the cartridge 116 of a patch pump system 100 according to an embodiment of the present invention.

Initially, the cartridge 116—unattached to the drive unit of the pump—is connected to a disposable plunger 174 and a vial adapter 176. As shown in FIG. 9A, the user then pulls outwardly on the disposable plunger 174 in the direction of the arrow to draw air into the cartridge 116. The vial adapter 176 is then connected to a vial 178 of medicament as shown in FIG. 9B and the disposable plunger is depressed in the direction of the arrow to expel the air that was drawn into the cartridge 116 into the vial 178. This cartridge filling assembly is then turned upside down as shown in FIG. 9C and the disposable plunger 174 is again pulled outwardly in the direction of the arrow to draw medicament from the vial 178 to fill the cartridge. The vial 178, vial adapter 176 and disposable plunger 174 are then disconnected from the cartridge 116 and the cartridge 116 is ready to be loaded onto a drive unit 118 of a pump as described herein.

Patch pumps according to embodiments of the present invention can include one or more rechargeable batteries in the drive unit. In some embodiments, a rechargeable battery can be inductively charged. FIGS. 10A-10E depict a procedure for inductively charging the one or more batteries of a patch pump according to one embodiment. Such an embodiment includes an inductive charging pad 180 as shown in FIG. 10A. To charge the pump 102, it is removed from attachment with the user's body (FIG. 10B) and/or disconnected from the tubing of the infusion set (FIG. 10C). The charging pad 180 can optionally include a cover 182 having a cutout sized to receive pump 102 in order to properly position and retain the pump 102 on the charging pad 180 such as is shown in FIG. 10D. The pump 102 can be placed onto the charging pad 180 as shown in FIG. 10E where it will automatically be inductively charged when the pad 180 is connected to a power source. In some embodiments, a patch pump that can be inductively charged does not include a connection, such as a USB port, into which a power cord can be inserted for power transfer. Such an embodiment provides the advantages of being more robust for waterproofing because of the lack of exposed electrical contacts and obviating electrical isolation requirements imposed upon such connections.

FIGS. 11A-11E depict one embodiment of a procedure for affixing the attachment portion 104 of a patch pump system to the skin of a user and inserting a cannula into the skin. First, an adhesive backing 107 can be removed from the adhesive patch 108 holding the retention frame 106 and the patch applied to the skin at the desired insertion site. Next, a cannula inserter 184 is aligned with the insertion portion 112 of retention frame 106 (see FIGS. 1A-1B) for insertion of a cannula into the user's skin. Proper alignment can be insured by inserting distally positioned feet 186 of the inserter 184 into slots in the retention frame 106 adjacent the insertion portion 112 as shown in FIGS. 11B and 11C. In some embodiments, feet 186 can include a hook portion that hooks into the slots to maintain the position of the feet 186 within slots during the insertion process. The inserter 184 is pushed down in the direction of the arrow as shown in FIG. 11D to insert the cannula 188 and then removed leaving the cannula 188 in place on the frame and inserted through the skin as shown in FIG. 11E. FIGS. 12A-12D show a substantially similar procedure for inserting a cannula into an infusion site located remotely from the pump such as is shown in FIG. 5A-5B, with an infusion site connector 148 and an infusion site patch 190 used in place of adhesive patch 107 with retention frame 106. In some embodiments, an audible sound such as a click sounding can indicate that the cannula has been properly inserted.

Figures 13A, 13B, 13C:
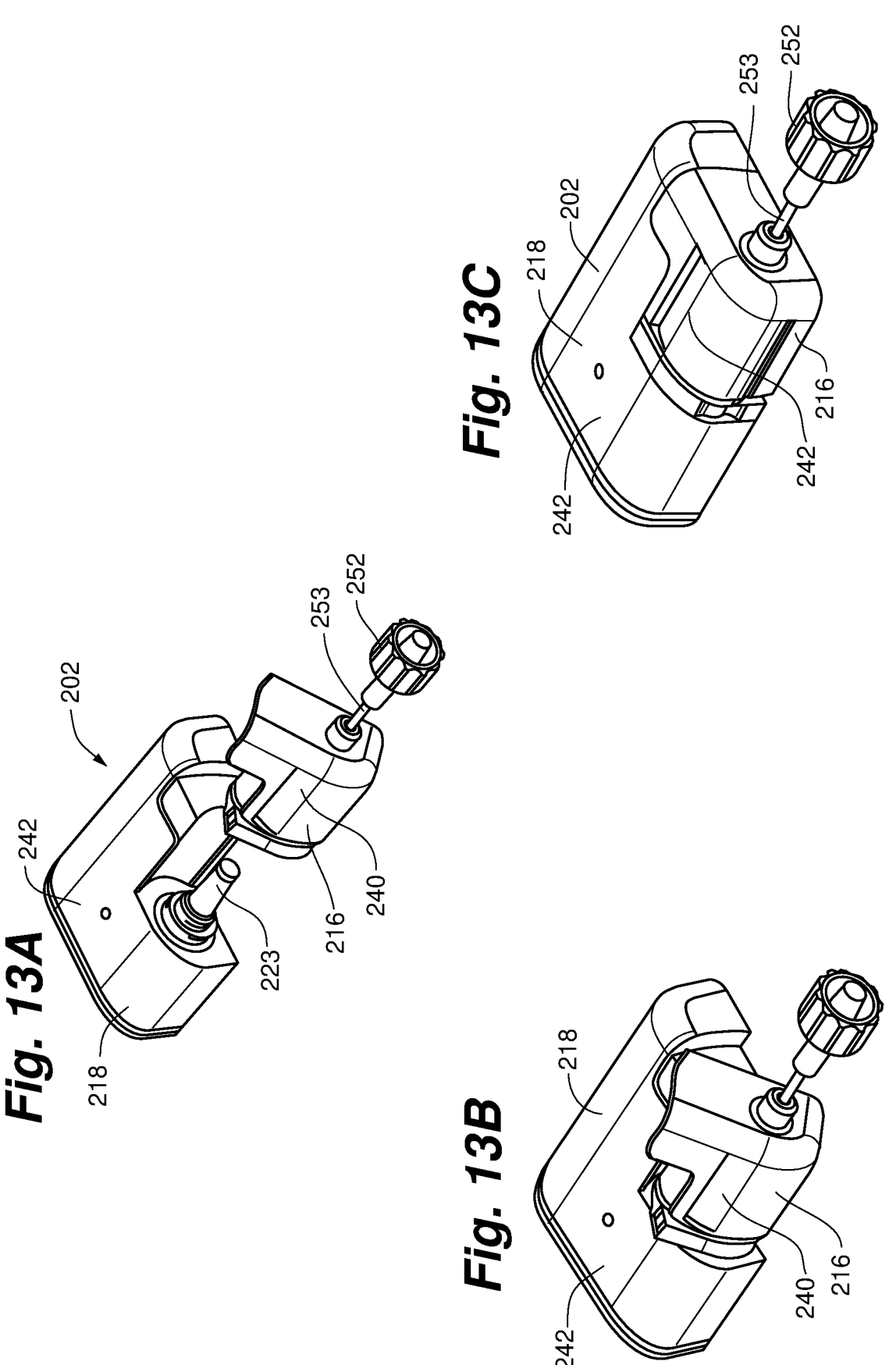
FIGS. 13A-13C depict a patch pump according to an embodiment of the present invention.

Referring now to FIGS. 13A-13C, a patch pump 202 that can be used with patch pump systems as described herein according to another embodiment of the invention is depicted. Patch pump 202 is similar to patch pump 102 in that cartridge 216 is attached to drive unit 218 by axially moving and rotating cartridge 216 with respect to drive unit 218. As shown in FIGS. 13A-13B, the drive end 223 of the drive mechanism 222 of the drive unit 218 is axially inserted into a recess (not pictured) in the cartridge 216 with the outer front housing surface 240 of the cartridge 216 at an offset, non-parallel angle to the outer front housing surface 242 of the drive unit 218 and then the cartridge 216 is rotated to attach and lock the cartridge 216 in place on the drive unit 218 with the front surfaces 240, 242 parallel as shown in FIG. 13C. In the depicted embodiment, the offset angle between the front surfaces 240, 242 at the initial attachment is approximately 60 degrees. The key aspect of such a rotation is that it enables locking features of the cartridge and drive unit to be initially aligned and then rotated into engagement with each other to lock the cartridge in place on the drive unit, which can be accomplished with a wide variety of angles in various embodiments. For example, in certain embodiments, this angle can be between about 30 degrees and about 150 degrees.

Figures 14A, 14B:
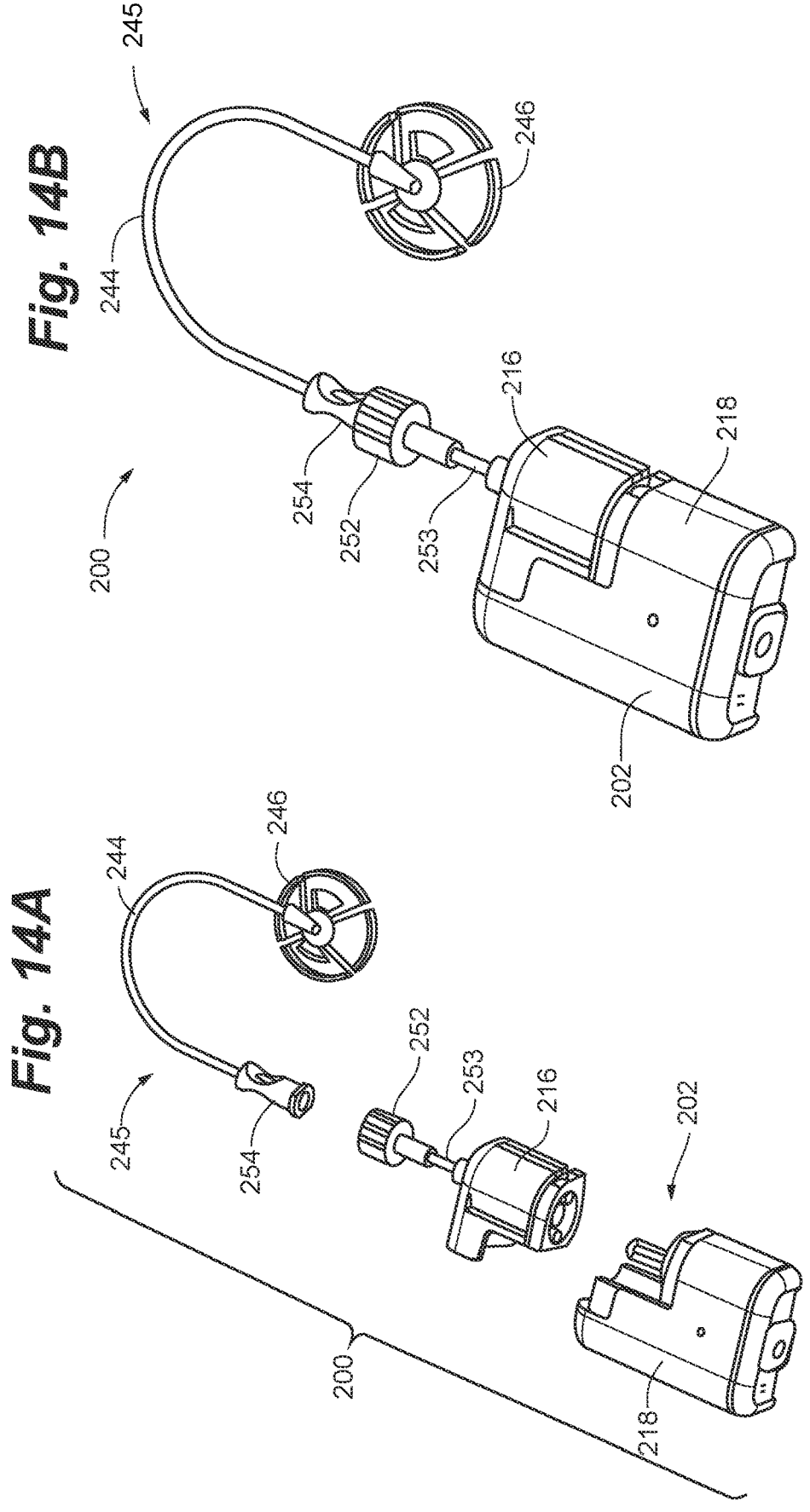
FIGS. 14A-14B depict a patch pump system according to an embodiment of the present invention.

Also depicted in the embodiment of FIGS. 13A-13C is a short length of tubing 253 and a connector 252. As can be seen in FIGS. 14A and 14B, connector 252 is designed to connect to a connector 254 of an infusion set 245. Infusion set 245 includes a length of tubing 244 extending from the connector 254 to a site connector 246 that connects to an infusion site connector as shown in, e.g., FIGS. 5A-5B to deliver medicament to the infusion site. In some embodiments, connector 252 extending from cartridge 216 and connector 254 of infusion set 245 can be Luer Lock connections.

Figure 15:
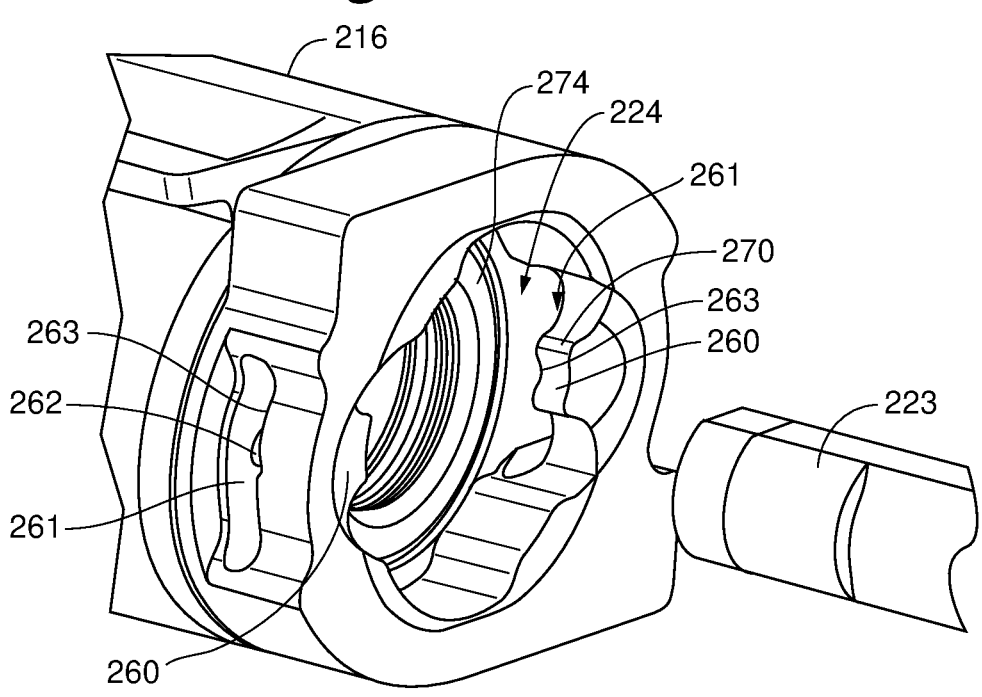
Figure 16:
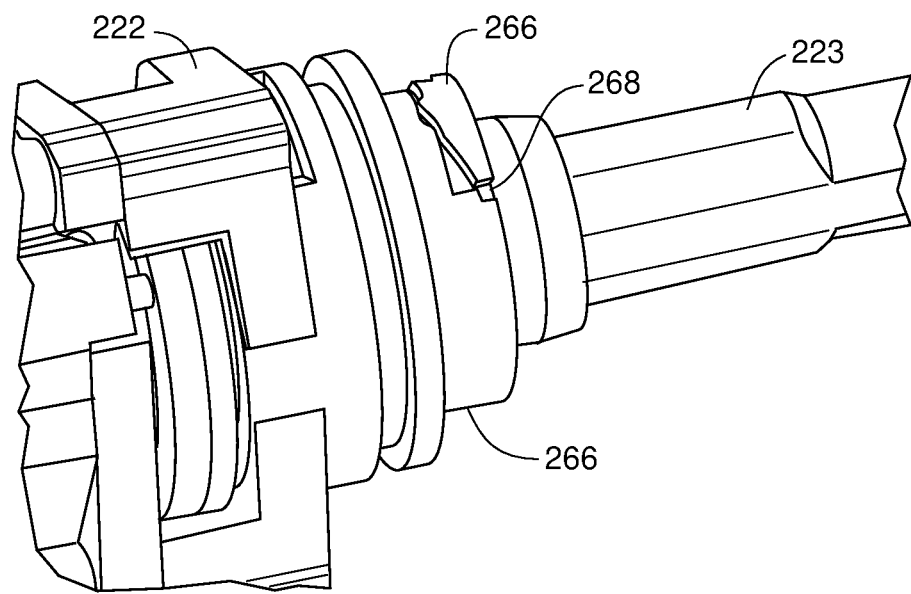

Further details regarding the connection features of the cartridge 216 and the drive unit 218 are shown in FIG. 15 and FIG. 16, respectively. As noted above, cartridge 216 includes a coupling recess 224 into which drive end 223 of drive unit 218 is inserted by relative axial motion between cartridge 216 and drive unit 218. Referring to FIG. 15, cartridge 216 defines a pair of slots 261 on opposing sides of recess 224 and a corresponding flange 260 located axially proximally of each slot 261 and projecting towards the center of recess 224. A detent groove 262 is positioned on a surface 263 that defines both a proximal surface of slot 261 and a distal surface of flange 260. Flange 260 further defines a convex stop feature 270. An o-ring 274 can also be positioned within recess 224 to enhance sealing between and reduce wear and tear on the components. As shown in FIG. 16, drive mechanism 222, shown without drive unit housing for sake of clarity, includes a pair of threads or locking wedges 266 configured to mate with the slots 261 defined in cartridge 216, as will be discussed in further detail below. Threads 266 each further define a concave stop feature 268 that can cooperate with stop feature 270 of cartridge 216 to ensure proper angular alignment of the cartridge 216 and drive unit 218, as will also be explained in further detail below. In some embodiments, threads or wedges, which could also be considered flanges, are flexible and elastically deform in order to form a proper connection.

As can be seen in FIGS. 17A-17B, threads 266 on drive mechanism 222 are provided with a geometry that closes matches the geometry of slots 261 in cartridge 216, including a detent projection 264 that matches the detent groove 262 in slot 261. The geometry of threads 266 differs from that of slots 261 in that each thread 266 is a wedge that increases in width from a leading edge of the thread 266 defined by the stop feature 268 towards the detent projection 264, whereas a width of the corresponding slot 261 remains generally constant. This narrower leading portion of the threads 266 enables the threads to easily be initially inserted into the slots 261 upon initial rotation of the cartridge 216 while providing a secure, compression fit as the wider portions of the threads 266 are forced into the slots 261 upon further rotation of the cartridge 216 relative to the drive mechanism 222. A curved ramp 272 is providing on a trailing end of each thread 266 to ease the removal of the threads 266 from the slots 261 by rotating the cartridge 216 in the opposite direction.

Figures 18A, 18B:
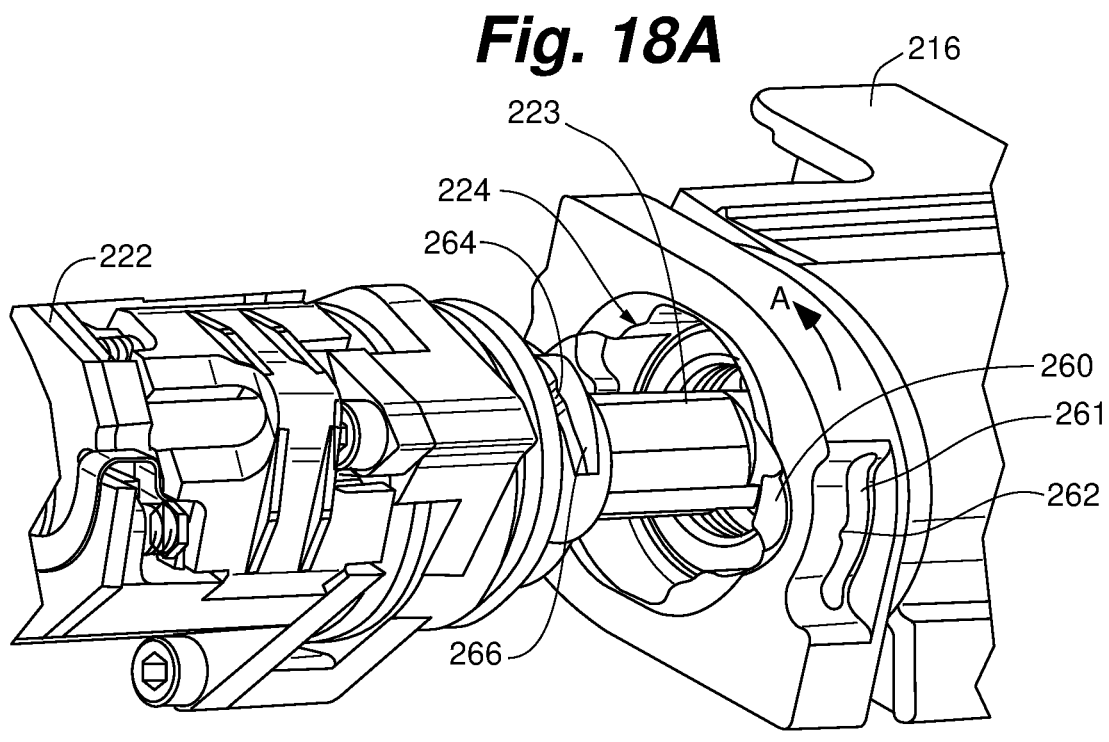

FIG. 18A depicts the proper angular orientation of cartridge 216 with respect to drive mechanism 222 for their relative axial movement to insert coupling recess 224 onto drive end 223, thereby enabling connection of the cartridge 216 and the drive unit 218. As can be seen in the figure, the threads 266 of drive mechanism 222 are rotationally offset from the slots 261 and flanges 260 in the recess 224 of cartridge 216. If the threads 266 are not offset, as shown in FIGS. 17A-17B, the flanges 260 would abut the threads 266 upon initial relative cartridge-drive mechanism relative axial movement, preventing further relative axial movement, which in turn prevents insertion of the drive end 223 further into the recess 223. In this manner, the flanges 260 serve to ensure proper angular orientation of the cartridge 216 with respect to the drive unit so to effect a proper connection therebetween. When a proper angular orientation is achieved, the drive mechanism 222 is inserted into the recess 223 until the threads 266 have been advanced axially distal of the flanges 260.

Figure 18C:
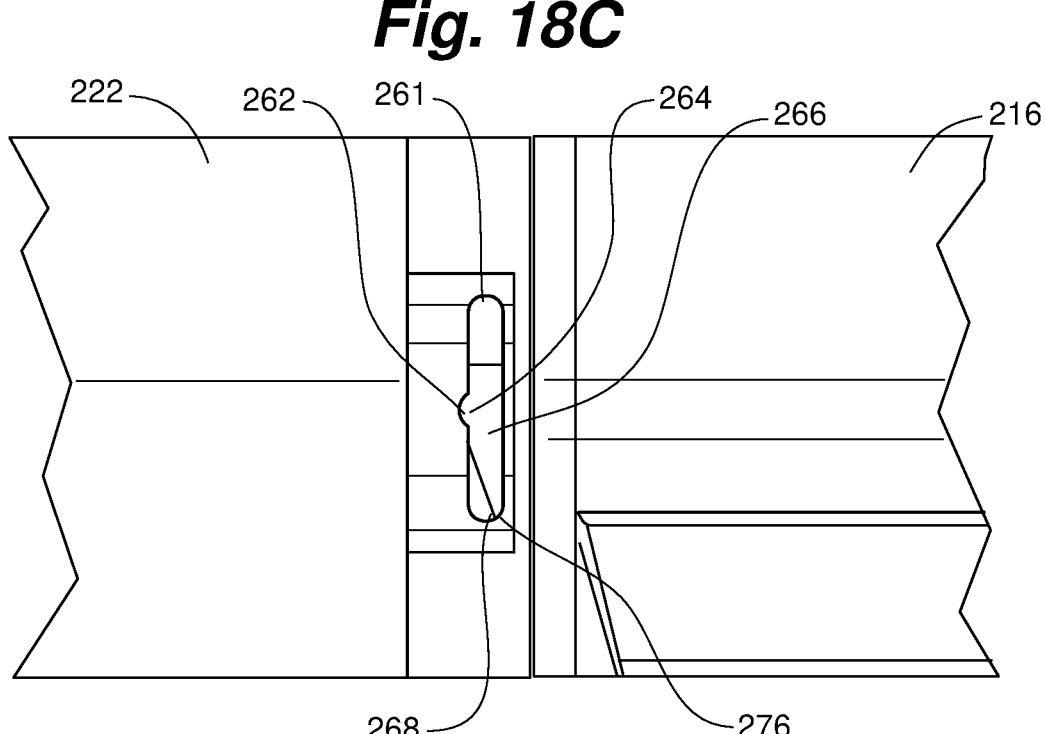

One the threads 266 have been axially aligned with slots 261, the cartridge 216 can now be rotated relative to drive mechanism 222, in the direction of the arrow A in FIGS. 18A-18B, to attach the cartridge 216 to the drive unit by mating the threads 266 with the slots 261. FIG. 18B depicts a thread 266 partially seated within a slot 261 after partial rotation of the cartridge 216 with respect to the drive unit. As can be seen in the figure, the narrower leading edge of thread defined by stop feature 268 has enabled initial insertion of the thread 266 into the slot 261 and a compression fit has begun to form as the wider portions of thread 266 are forced into the slot 261. This rotation continues until the detent projections 264 on threads 266 are seated in the detent grooves 262 in slots 261 as shown in FIG. 18C, at which point the cartridge 216 is aligned flush with drive unit and the cartridge is prevented from further rotation by the leading edge of threads 266 abutting the ends 276 of the slots and the detent projections 264 nested in the detent slots 262. The cartridge 216 cannot be distally moved away from the drive unit by the threads 266 being confined by the slots 261 and the flanges 260. Curved ramp portions 272 of threads 266 are also held within slots 261 to retain the cartridge 216 in place, but rotation of the cartridge in the opposite direction of the insertion direction with a requisite amount of force to slide the detent projections 264 out of the detent grooves 262 will cause curved ramp portions 272 to slide out of slots 216 to enable disengagement of the cartridge 216 from the drive unit.

Figure 19:
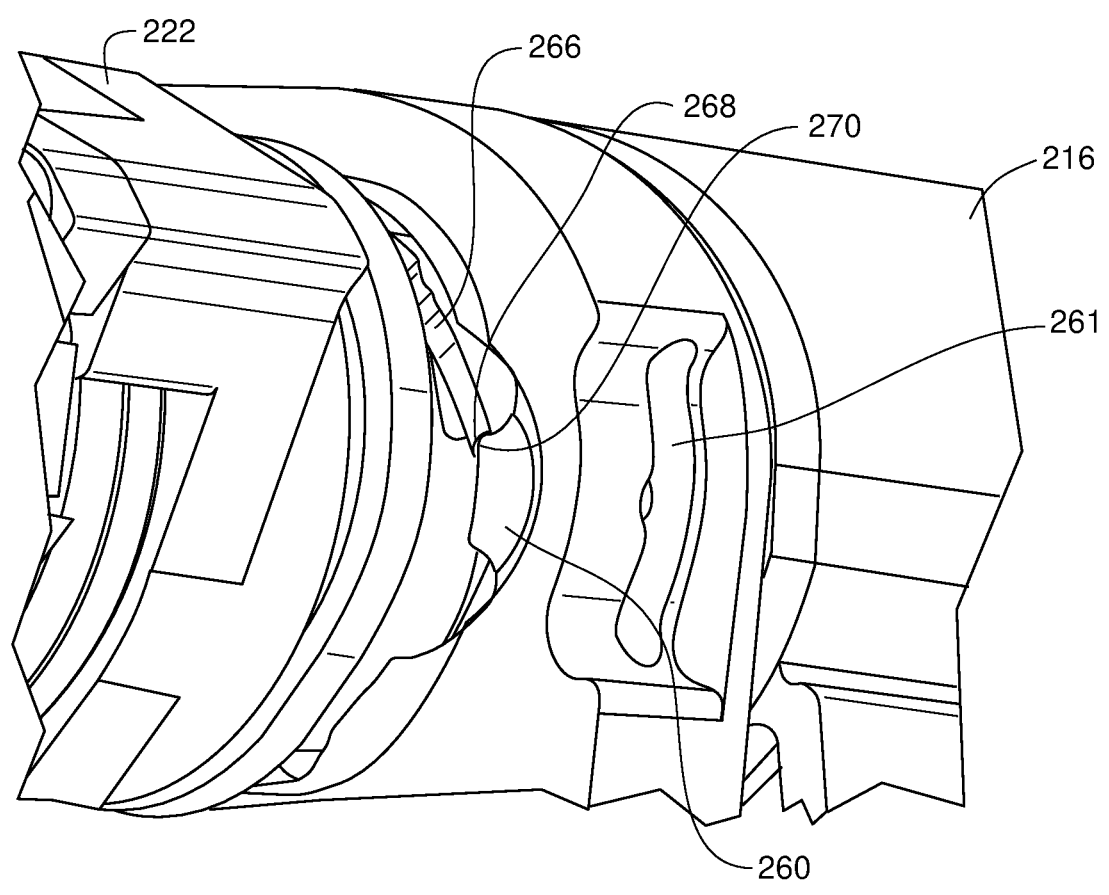

FIG. 19 depicts the operation of stop features 268 and 270, which function to ensure that the drive mechanism 222 is inserted to the proper axial depth into recess 224 before the cartridge 216 is rotated. If the drive mechanism 222 is not inserted into the recess 224 such that the flanges 260 are advanced axially past the threads 266 to align the threads 260 with the slots 261, when the cartridge 216 is rotated the stop features 168 at the leading edges of the threads 266 will encounter the stop features 270 of the flanges 260. This prevents further rotation of the cartridge 216 relative to drive unit 218. The convex mating configuration of the stop features 270 of the flanges 260 and concave configuration of the stop features 268 of the threads 266, which, in certain embodiments, can be reversed or shaped differently, ensure that repeated contact between these components will not unreasonably stress or wear on the components.

After the cartridge has been installed on the drive unit according to the embodiments of the invention described herein, the cartridge is retained on the drive unit with sufficient force to minimize any compliance in the connection. As such, manufacturing tolerances for the flanges features on the disclosed cartridges are such that at the extents of the manufacturing tolerances the flanges flex with enough force upon the cartridge being installed onto the drive unit that when the drive mechanism is operated to push against a plunger in the cartridge to dispense medicament from the cartridge, there is no relative movement between the cartridge and the drive system. In one embodiment, the nominal flex or interference of the cartridge flanges is about 0.010 inches with a range due to tolerance stacking of about 0.006 to 0.014 inches. This enables the attachment to be sufficient to withstand force values of approximately 5 to 12 pounds, which in some embodiments is the maximum force output of the drive mechanism and equates to infusion pressures of approximately 20-50 psi. A benefit of minimizing this compliance is that it decreases the time to detect occlusions that are detected based on the motor stalling and minimizes the bolus a patient receives if an occlusion in the tubing is cleared to the pressure increase.

Although the pump system described herein is described as a user-wearable patch pump system that has no display or user interface and is primarily controlled by a remote device, it should be understood that aspects of the present disclosure can be incorporated into other types of infusion pumps. For example, full-featured user-wearable infusion pumps having display and input capabilities, such as a touchscreen display on the pump housing, such as disclosed in U.S. Pat. No. 8,287,495, which is hereby incorporated by reference herein, can incorporate aspects of the present disclosure.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; and 9,335,910 commonly owned U.S. Patent Publication Nos. 2009/0287180; 2012/0123230; 2013/0053816; 2013/0159456; 2013/0324928; 2013/0331790; 2013/0332874; 2014/0273042; 2014/0276419; 2014/0276420; 2014/0276423; 2014/0276531; 2014/0276537; 2014/0276553; 2014/0276556 2014/0276569; 2014/0276570; 2014/0276574; 2014/0378898; 2015/0073337; 2015/0072613; 2015/0182693; 2015/0182694; 2015/0182695; 2016/0030669; and 2016/0082188 and commonly owned U.S. patent application Ser. No. 14/707,851 and commonly owned U.S. Provisional Application Ser. Nos. 61/911,576; 61/920,902; 61/920,914; 61/920,940; 62/139,275; 62/163,158; 62/207, 748; 62/256,398; 62/272,255 and 62/300,410.

Further incorporated by reference herein in their entirety are U.S. Pat. Nos. 8,601,465; 8,502,662; 8,452,953; 8,451, 230; 8,449,523; 8,444,595; 8,343,092; 8,285,328; 8,126, 728; 8,117,481; 8,095,123; 7,999,674; 7,819,843; 7,782, 192; 7,109,878; 6,997,920; 6,979,326; 6,936,029; 6,872, 200; 6,813,519; 6,641,533; 6,554,798; 6,551,276; 6,295, 506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A user-wearable infusion pump system, comprising:
a user-wearable infusion pump including a bolus input and no display;
a retention frame having a perimeter shape generally matching a perimeter shape of the user-wearable infusion pump configured to releasably lock the user-wearable infusion pump thereon;
an adhesive patch attached to the retention frame to adhere the retention frame to a body of a user;
a remote control device configured to establish a connection with the user-wearable infusion pump; and
infusion tubing extending from the user-wearable infusion pump with a connector at a distal end of the infusion tubing, wherein the connector is configured to attach to an end connector of an infusion set having tubing extending from the end connector to an infusion site connector configured to facilitate delivery of medicament from the user-wearable infusion pump to an infusion site remote from the user-wearable infusion pump, wherein the connector is in fluid communication with a medicament reservoir of the user-wearable infusion pump to facilitate refilling the reservoir with medicament,
wherein the user-wearable infusion pump comprises a drive unit and a medicament cartridge including the reservoir selectively attachable to the drive unit, and
wherein the medicament cartridge is configured to be inserted onto the drive unit in a first orientation with a front surface and a rear surface of the medicament cartridge in a non-parallel orientation with a front surface and a rear surface of the drive unit and to be rotated less than 360 degrees to selectively lock the medicament cartridge onto the drive unit with the front surface and the rear surface of the medicament cartridge being in a generally parallel orientation with the front surface and the rear surface of the drive unit.

2. The system of claim 1, wherein the connection between the user-wearable infusion pump and the remote control device is established over one of Bluetooth, Bluetooth low energy, mobile, or Wi-Fi communication.

3. The system of claim 1, wherein the remote control device is a smartphone.

4. The system of claim 1, wherein the remote control device is a wearable electronic watch.

5. The system of claim 1, wherein the remote control device is one of an electronic health and fitness monitor, a personal digital assistant, a tablet, a laptop, or a personal computer.

6. The system of claim 1, wherein the remote control device is a dedicated remote controller designed for use with the user-wearable infusion pump.

7. The system of claim 6, wherein the dedicated remote controller further comprises one or more of a speaker, a microphone, a vibrator, or a light for providing alerts, alarms, and notifications.

8. The system of claim 1, wherein the user-wearable infusion pump is configured to be interchangeably used with the retention frame and adhesive patch to deliver medicament to an infusion site beneath the retention frame and the infusion set to deliver medicament to the infusion site remote from the user-wearable infusion pump.

9. The system of claim 1, wherein the user-wearable infusion pump includes a processor configured to:
receive input to initiate delivery of medicament via the bolus input;
initiate dosing of medicament in response to the input received via the bolus input; and
in response to initiating dosing of medicament in response to the input received via the bolus input, transfer feedback regarding the dosing of medicament initiated in response to the input received via the bolus input from the user-wearable infusion pump to the remote control device for presentation on a display screen of the remote control device.

10. The system of claim 9, wherein the feedback further comprises information from a glucose meter interfacing with the user-wearable infusion pump.

11. The system of claim 9, wherein the feedback further comprises information regarding the status of the user-wearable infusion pump.

12. The system of claim 1, wherein the reservoir is configured to be refilled via the connector when the medicament cartridge is detached from the drive unit.

13. The system of claim 12, further comprising a vial adapter configured to connect the medicament cartridge to a medicament vial to facilitate refilling of the reservoir with medicament from the medicament vial.

14. A user-wearable infusion pump system, comprising:
a user-wearable infusion pump including a bolus input and no display, the user-wearable infusion pump having a length of tubing with a connector extending therefrom, wherein the connector is in fluid communication with a medicament reservoir of the user-wearable infusion pump to facilitate refilling the reservoir with medicament;
a retention frame having a perimeter shape generally matching a perimeter shape of the user-wearable infusion pump configured to releasably lock the user-wearable infusion pump thereon;
an adhesive patch attached to the retention frame to adhere the retention frame to a body of a user; and
a remote control device configured to establish a connection with the user-wearable infusion pump; and
an infusion set including an end connector configured to attach to the connector of the user-wearable infusion pump and infusion tubing extending from the end connector to an infusion site connector, wherein the infusion set is configured to facilitate delivery of medicament from the user-wearable infusion pump to an infusion site coupled with the infusion site connector remote from the user-wearable infusion pump, wherein the user-wearable infusion pump comprises a drive unit and a medicament cartridge including the reservoir selectively attachable to the drive unit, and
wherein the medicament cartridge is configured to be inserted onto the drive unit in a first orientation with a front surface and a rear surface of the medicament cartridge in a non-parallel orientation with a front surface and a rear surface of the drive unit and to be rotated less than 360 degrees to selectively lock the medicament cartridge onto the drive unit with the front surface and the rear surface of the medicament cartridge being in a generally parallel orientation with the front surface and the rear surface of the drive unit.

15. The system of claim 14, wherein the user-wearable infusion pump is configured to be interchangeably used with the retention frame and adhesive patch to deliver medicament to an infusion site beneath the retention frame and the infusion set to deliver medicament to the infusion site remote from the user-wearable infusion pump.

16. The system of claim 14, wherein the reservoir is configured to be refilled via the connector when the medicament cartridge is detached from the drive unit.

17. The system of claim 16, further comprising a vial adapter configured to connect the medicament cartridge to a medicament vial to facilitate refilling of the reservoir with medicament from the medicament vial.

* * * * *